(12) United States Patent
Hubert et al.

(10) Patent No.: US 6,835,822 B1
(45) Date of Patent: Dec. 28, 2004

(54) DIAGNOSIS AND THERAPY OF CANCER USING SGP28-RELATED MOLECULES

(75) Inventors: Rene S. Hubert, Los Angeles, CA (US); Arthur B. Raitano, Los Angeles, CA (US); Daniel E. H. Afar, Brisbane, CA (US); Steve Chappell Mitchell, Santa Monica, CA (US); Mary Faris, Los Angeles, CA (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 70 days.

(21) Appl. No.: 09/698,781

(22) Filed: Oct. 27, 2000

Related U.S. Application Data
(60) Provisional application No. 60/162,610, filed on Oct. 28, 1999.

(51) Int. Cl.$^7$ .............................................. C07H 21/04
(52) U.S. Cl. ...................... 536/23.5; 530/300; 530/350; 536/23.1; 536/24.31; 536/24.33; 424/185.1
(58) Field of Search .......................... 536/24.31, 24.33, 536/23.1, 23.5; 530/300; 424/185.1

(56) References Cited

FOREIGN PATENT DOCUMENTS

WO  WO 99/06550  2/1999

OTHER PUBLICATIONS

Shastri N, et al. Annu Rev Immunol. 2002; 20: 463–93.*
Gura T. Science. 1997; 278: 1041–2.*
Bodey B, et al. Anticancer Res. 2000; 20: 2665–76.*
Splitler LE. Cancer Biotherapy, 1995; 10(1): 1–3.*
Ezzell C. J NIH Res. Jan. 1995; 7: 46–9.*
Bergers G, et al. Curr Opin Genetics Develop. 2000; 10: 120–7.*
Cox AL, et al. Science 1994; 264: 716–9.*
Precup JW, et al. Blood May 1, 1991; 77 (9): 1929–36.*
Skolnick J, et al. Trends Biotechnol Jan. 2000; 18 (1): 34–9.*
Ahn AH, et al. Nat Genet Apr. 1993; 3 (4): 283–91.*
Burgess WH, et al. J Cell Biol Nov. 1990; 111 (5 Pt 1): 2129–38.*
Bowie JU, et al. Science Mar. 16, 1990; 247 (4948): 1306–10.*
Lazar E, et al. Mol Cell Biol Mar. 1988; 8 (3): 1247–52.*
J. Kratzschmar et al., "The human cystein–rich secretory protein (CRISP) family Primary structure and tissue distribution of CRISP–1, CRISP–2 and CRISP–3," 1996, XP–000997999, Eur. J. Biochem. 236:827–836.
L. Kjeldsen et al., "SGP28, a novel matrix glycoprotein in specific granules of human neutrophils with similarity to a human testis–specific gene product and to a roden sperm–coating glycoprotein," 1996, XP–000993086, FEBS Letters 380:246–250.
M. Harding, "Prognostic markers in localized prostate cancer: From microscopes to molecules," 1999, XP–000997993, Cancer and Metastasis Reviews, 17:429–437.
X. Gao et al., "Diagnostic and Prognostic Markers for Human Prostate Cancer," 1997, XP–000998020, The Prostate, 31:264–281.
J.T. Isaacs, "Molecular Markers for Prostate Cancer Metastasis," 1997, XP–000997986, American Jounal of Pathology, 150(5):1511–1521.
J. Kratzschmar et al., Apr. 12, 1996, GenBank Accession No. X95240.
L. Kjeldsen, Nov. 1, 2000, GenBank Accession No. NM_006061.
L. Kjeldsen et al., Mar. 4, 1996, GenBank Accession No. X94323.
L. Kjeldsen et al., Nov. 1, 2000, GenBank Accession No. NP_006052.
L. Kjeldsen e tal., Jun. 20, 2000, GenBank Accession No. S68691.

* cited by examiner

*Primary Examiner*—Yvonne Eyler
*Assistant Examiner*—Stephen L. Rawlings
(74) *Attorney, Agent, or Firm*—Morrison & Foerster LLP

(57) ABSTRACT

The present invention relates to methods and compositions for the diagnosis and therapy of prostate cancer which utilize isolated polynucleotides corresponding to the human SGP28 gene, proteins encoded by the SGP28 gene and fragments thereof, and antibodies capable of specifically recognizing and binding to SGP28 proteins.

6 Claims, 10 Drawing Sheets

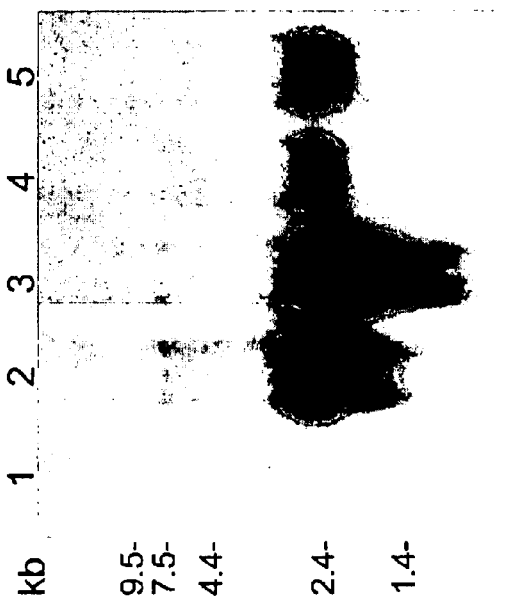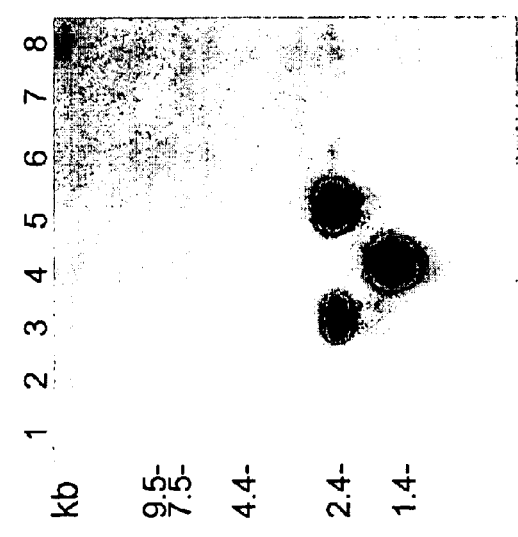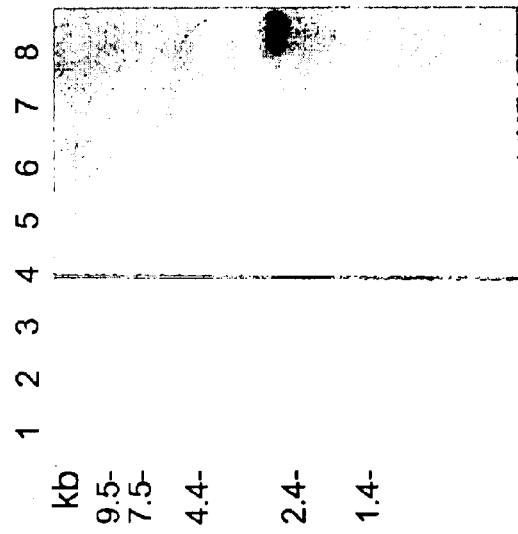

FIG. 8C PIN
FIG. 8D
FIG. 8A Prostate cancer
200X
FIG. 8B
800X

SEQUENCE LISTING

```
<160> NUMBER OF SEQ ID NOS:  36

<210> SEQ ID NO 1
<211> LENGTH: 256
<212> TYPE: DNA
<213> ORGANISM: Homo Sapiens

<400> SEQUENCE: 1
gatctctata gtaactgtaa aagtttgaag ctcacattaa cctgtaaaca tcagttggtc      60
agggacagtt gcaaggcctc ctgcaattgt tcaaacagca tttattaaat acgcattaca     120
caccgagtag ggctatgtag agaggagtca gattatctac ttagatttgg catctactta     180
gatttaacat atactagctg agaaattgta ggcatgtttg atacacattt gatttcaaat     240 gttttcttc tggatc                                                       256

<210> SEQ ID NO 2
<211> LENGTH: 2144
<212> TYPE: DNA
<213> ORGANISM: Homo Sapiens

<400> SEQUENCE: 2
tgatgaaaca aatacttcat cctgctctgg aaaccactgc aatgacatta ttcccagtgc      60
tgttgttcct ggttgctggg ctgcttccat cttttccagc aaatgaagat aaggatcccg     120
cttttactgc tttgttaacc acccaaacac aagtgcaaag ggagattgtg aataagcaca     180
atgaactgag gagagcagta tctcccctg ccagaaacat gctgaagatg gaatggaaca     240
aagaggctgc agcaaatgcc caaaagtggg caaaccagtg caattacaga cacagtaacc     300
caaaggatcg aatgacaagt ctaaatgtg gtgagaatct ctacatgtca agtgccccca     360
gctcatggtc acaagcaatc caaagctggt ttgatgagta caatgatttt gactttggtg     420
tagggccaaa gactcccaac gcagtggttg gacattatac acaggttgtt tggtactctt     480
catacctcgt tggatgtgga aatgcctact gtcccaatca aaaagttcta aaatactact     540
atgtttgcca atattgtcct gctggtaatt gggctaatag actatatgtc ccttatgaac     600
aaggagcacc ttgtgccagt tgcccagata actgtgacga tggactatgc accaatggtt     660
```

-continued

```
gcaagtacga agatctctat agtaactgta aaagtttgaa gctcacatta acctgtaaac    720
atcagttggt cagggacagt tgcaaggcat cctgcaattg ttcaaacagc atttattaaa    780
tacgcattac acaccgagta gggctatgta gagaggagtc agattatcta cttagatttg    840
gcatctactt agatttaaca tatactagct gagaaattgt aggcatgttt gatacacatt    900
tgatttcaaa tgttttctt ctggatctgc tttttatttt acaaaaatat ttttcataca     960
aatggttaaa agaaacaaa atctataaca acaactttgg attttatat ataaactttg     1020
tgatttaaat ttactgaatt taattagggt gaaaattttg aaagttgtat ctctcatatga  1080
ctaagttcac taaaaccctg gattgaaagt gaaaattatg ttcctagaac aaaatgtaca   1140
aaaagaacaa tataatttc acatgaaccc ttggctgtag ttgcctttcc tagctccact    1200
ctaaggctaa gcatcttcaa agacgttttc ccatatgctg tcttaattct tttcactcat   1260
tcacccttct tcccaatcat ctggctggca tcctcacaat tgagttgaag ctgttcctcc   1320
taaaacaatc ctgactttta ttttgccaaa atcaatacaa tcctttgaat ttttatctg    1380
cataaatttt acagtagaat atgatcaaac cttcattttt aaacctctct tctctttgac   1440
aaaacttcct taaaaaagaa tacaagataa tataggtaaa taccctccac tcaaggaggt   1500
agaactcagt cctctcccctt gtgagtcttc actaaaatca gtgactcact tccaaagagt   1560
ggagtatgga aagggaaaca tagtaacttt acaggggaga aaaatgacaa atgacgtctt   1620
caccaagtga tcaaaattaa cgtcaccagt gataagtcat tcagatttgt tctagataat   1680
ctttctaaaa attcataatc ccaatctaat tatgagctaa aacatccagc aaactcaagt   1740
tgaaggacat tctacaaaat atccctgggg tattttagag tattcctcaa aactgtaaaa   1800
atcatggaaa ataagggaat cctgagaaac aatcacagac cacatgagac taaggagaca   1860
tgtgagccaa atgcaatgtg cttcttggat cagatcctgg aacagaaaaa gatcagtaat   1920
gaaaaactg atgaagtctg aatagaatct ggagtatttt taacagtagt gttgatttct    1980
taatcttgac aaatatagca gggtaatgta agatgataac gttagagaaa ctgaaactgg   2040
gtgagggcta tctaggaatt ctctgtacta tcttaccaaa ttttcggtaa gtctaagaaa   2100
gcaatgcaaa ataaaagta tcttgaaaaa aaaaaaaaa aaaa                      2144
```

<210> SEQ ID NO 3
<211> LENGTH: 258
<212> TYPE: PRT
<213> ORGANISM: Homo Sapiens

<400> SEQUENCE: 3

```
Met Lys Gln Ile Leu His Pro Ala Leu Glu Thr Thr Ala Met Thr Leu
 1               5                  10                  15

Phe Pro Val Leu Leu Phe Leu Val Ala Gly Leu Leu Pro Ser Phe Pro
            20                  25                  30

Ala Asn Glu Asp Lys Asp Pro Ala Phe Thr Ala Leu Leu Thr Thr Gln
        35                  40                  45

Thr Gln Val Gln Arg Glu Ile Val Asn Lys His Asn Glu Leu Arg Arg
    50                  55                  60

Ala Val Ser Pro Pro Ala Arg Asn Met Leu Lys Met Glu Trp Asn Lys
65                  70                  75                  80

Glu Ala Ala Ala Asn Ala Gln Lys Trp Ala Asn Gln Cys Asn Tyr Arg
                85                  90                  95

His Ser Asn Pro Lys Asp Arg Met Thr Ser Leu Lys Cys Gly Glu Asn
            100                 105                 110
```

-continued

```
Leu Tyr Met Ser Ser Ala Pro Ser Ser Trp Ser Gln Ala Ile Gln Ser
            115                 120                 125

Trp Phe Asp Glu Tyr Asn Asp Phe Asp Phe Gly Val Gly Pro Lys Thr
    130                 135                 140

Pro Asn Ala Val Val Gly His Tyr Thr Gln Val Val Trp Tyr Ser Ser
145                 150                 155                 160

Tyr Leu Val Gly Cys Gly Asn Ala Tyr Cys Pro Asn Gln Lys Val Leu
                165                 170                 175

Lys Tyr Tyr Val Cys Gln Tyr Cys Pro Ala Gly Asn Trp Ala Asn
            180                 185                 190

Arg Leu Tyr Val Pro Tyr Glu Gln Gly Ala Pro Cys Ala Ser Cys Pro
            195                 200                 205

Asp Asn Cys Asp Asp Gly Leu Cys Thr Asn Gly Cys Lys Tyr Glu Asp
210                 215                 220

Leu Tyr Ser Asn Cys Lys Ser Leu Lys Leu Thr Leu Thr Cys Lys His
225                 230                 235                 240

Gln Leu Val Arg Asp Ser Cys Lys Ala Ser Cys Asn Cys Ser Asn Ser
            245                 250                 255

Ile Tyr
```

```
<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
agttgccttt cctagctcca ctct                                          24

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5 tcccttttcca tactccactc tttg                                         24

<210> SEQ ID NO 6
<211> LENGTH: 11
<212> TYPE: PRT
<213> ORGANISM: Homo Sapiens

<400> SEQUENCE: 6

Val Val Gly His Tyr Thr Gln Val Val Trp Tyr
 1               5                  10

<210> SEQ ID NO 7
<211> LENGTH: 12
<212> TYPE: PRT
<213> ORGANISM: Homo Sapiens

<400> SEQUENCE: 7

Tyr Tyr Val Cys Gln Tyr Cys Pro Ala Gly Asn Trp
 1               5                  10

<210> SEQ ID NO 8
<211> LENGTH: 4
<212> TYPE: PRT
```

```
<213> ORGANISM: Homo Sapiens

<400> SEQUENCE: 8

Asn Cys Ser Asn
 1

<210> SEQ ID NO 9
<211> LENGTH: 4
<212> TYPE: PRT
<213> ORGANISM: Homo Sapiens

<400> SEQUENCE: 9

Ser Trp Phe Asp
 1

<210> SEQ ID NO 10
<211> LENGTH: 4
<212> TYPE: PRT
<213> ORGANISM: Homo Sapiens

<400> SEQUENCE: 10

Ser Cys Pro Asp
 1

<210> SEQ ID NO 11
<211> LENGTH: 7
<212> TYPE: PRT
<213> ORGANISM: Homo Sapiens

<400> SEQUENCE: 11

Lys Cys Gly Glu Asn Leu Tyr
 1               5

<210> SEQ ID NO 12
<211> LENGTH: 6
<212> TYPE: PRT
<213> ORGANISM: Homo Sapiens

<400> SEQUENCE: 12

Gly Leu Leu Pro Ser Phe
 1               5

<210> SEQ ID NO 13
<211> LENGTH: 6
<212> TYPE: PRT
<213> ORGANISM: Homo Sapiens

<400> SEQUENCE: 13

Gly Cys Gly Asn Ala Tyr
 1               5

<210> SEQ ID NO 14
<211> LENGTH: 6
<212> TYPE: PRT
<213> ORGANISM: Homo Sapiens

<400> SEQUENCE: 14

Gly Asn Trp Ala Asn Arg
 1               5

<210> SEQ ID NO 15
<211> LENGTH: 6
<212> TYPE: PRT
<213> ORGANISM: Homo Sapiens
```

```
<400> SEQUENCE: 15

Gly Ala Pro Cys Ala Ser
1               5

<210> SEQ ID NO 16
<211> LENGTH: 6
<212> TYPE: PRT
<213> ORGANISM: Homo Sapiens

<400> SEQUENCE: 16

Gly Leu Cys Thr Asn Gly
1               5

<210> SEQ ID NO 17
<211> LENGTH: 9
<212> TYPE: PRT
<213> ORGANISM: Homo Sapiens

<400> SEQUENCE: 17

Thr Leu Phe Pro Val Leu Leu Phe Leu
1               5

<210> SEQ ID NO 18
<211> LENGTH: 9
<212> TYPE: PRT
<213> ORGANISM: Homo Sapiens

<400> SEQUENCE: 18

Val Leu Leu Phe Leu Val Ala Gly Leu
1               5

<210> SEQ ID NO 19
<211> LENGTH: 9
<212> TYPE: PRT
<213> ORGANISM: Homo Sapiens

<400> SEQUENCE: 19

Ala Leu Leu Thr Thr Gln Thr Gln Val
1               5

<210> SEQ ID NO 20
<211> LENGTH: 9
<212> TYPE: PRT
<213> ORGANISM: Homo Sapiens

<400> SEQUENCE: 20

Val Val Trp Tyr Ser Ser Tyr Leu Val
1               5

<210> SEQ ID NO 21
<211> LENGTH: 9
<212> TYPE: PRT
<213> ORGANISM: Homo Sapiens

<400> SEQUENCE: 21

Thr Leu Thr Cys Lys His Gln Leu Val
1               5

<210> SEQ ID NO 22
<211> LENGTH: 9
<212> TYPE: PRT
<213> ORGANISM: Homo Sapiens

<400> SEQUENCE: 22
```

Gly Asn Trp Ala Asn Arg Leu Tyr Val
1               5

<210> SEQ ID NO 23
<211> LENGTH: 9
<212> TYPE: PRT
<213> ORGANISM: Homo Sapiens

<400> SEQUENCE: 23

Leu Leu Phe Leu Val Ala Gly Leu Leu
1               5

<210> SEQ ID NO 24
<211> LENGTH: 9
<212> TYPE: PRT
<213> ORGANISM: Homo Sapiens

<400> SEQUENCE: 24

Gln Val Val Trp Tyr Ser Ser Tyr Leu
1               5

<210> SEQ ID NO 25
<211> LENGTH: 9
<212> TYPE: PRT
<213> ORGANISM: Homo Sapiens

<400> SEQUENCE: 25

Ala Val Val Gly His Tyr Thr Gln Val
1               5

<210> SEQ ID NO 26
<211> LENGTH: 9
<212> TYPE: PRT
<213> ORGANISM: Homo Sapiens

<400> SEQUENCE: 26

Asp Leu Tyr Ser Asn Cys Lys Ser Leu
1               5

<210> SEQ ID NO 27
<211> LENGTH: 15
<212> TYPE: PRT
<213> ORGANISM: Homo Sapiens

<400> SEQUENCE: 27

Cys Asn Tyr Arg His Ser Asn Pro Lys Asp Arg Met Thr Ser Leu
1               5                   10                  15

<210> SEQ ID NO 28
<211> LENGTH: 14
<212> TYPE: DNA
<213> ORGANISM: Artificial Sequence
<220> FEATURE:
<223> OTHER INFORMATION: Primer

<400> SEQUENCE: 28
ttttgatcaa gctt                                              14

<210> SEQ ID NO 29
<211> LENGTH: 42
<212> TYPE: DNA
<213> ORGANISM: Artificial Sequence
<220> FEATURE:
<223> OTHER INFORMATION: Primer

<400> SEQUENCE: 29

-continued

```
ctaatacgac tcactatagg gctcgagcgg ccgcccgggc ag                          42

<210> SEQ ID NO 30
<211> LENGTH: 12
<212> TYPE: DNA
<213> ORGANISM: Artificial Sequence
<220> FEATURE:
<223> OTHER INFORMATION: Primer

<400> SEQUENCE: 30
ggcccgtcct ag                                                           12

<210> SEQ ID NO 31
<211> LENGTH: 40
<212> TYPE: DNA
<213> ORGANISM: Artificial Sequence
<220> FEATURE:
<223> OTHER INFORMATION: Primer

<400> SEQUENCE: 31
gtaatacgac tcactatagg gcagcgtggt cgcggccgag                             40

<210> SEQ ID NO 32
<211> LENGTH: 10
<212> TYPE: DNA
<213> ORGANISM: Artificial Sequence
<220> FEATURE:
<223> OTHER INFORMATION: Primer

<400> SEQUENCE: 32
cggctcctag                                                              10

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
ctaatacgac tcactatagg gc                                                22

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
tcgagcggcc gcccgggcag ga                                                22

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
agcgtggtcg cggccgagga                                                   20

<210> SEQ ID NO 36
<211> LENGTH: 24
<212> TYPE: DNA
```

```
-continued

<213> ORGANISM: FLAG Sequence

<400> SEQUENCE: 36
gattacaagg atgacgacga taag                                              24
```

DIAGNOSIS AND THERAPY OF CANCER USING SGP28-RELATED MOLECULES

This application claims the benefit of U.S. provisional patent application No. 60/162,610, filed Oct. 28, 1999, the entire contents of which are incorporated herein by reference.

FIELD OF THE INVENTION

The invention described herein relates to methods and compositions for the diagnosis and therapy of cancer, including prostate cancer, utilizing isolated polynucleotides, polypeptides, antibodies, and related molecules that correspond to or are reactive with human SGP28/CRISP-3.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Many cancer patients experience a recurrence.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease— second only to lung cancer. Despite the magnitude of these figures, there is still no effective treatment for metastatic prostate cancer. Surgical prostatectomy, radiation therapy, hormone ablation therapy, and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the management of this disease. Although the serum PSA assay has been a very useful tool, its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic disease progression, including the transition from androgen dependence to androgen independence and the development of metastatic lesions (Klein et al., 1997, Nat. Med. 3:402). More recently identified prostate cancer markers include PCTA-1 (Su et al., 1996, Proc. Natl. Acad. Sci. USA 93: 7252), prostate stem cell antigen (PSCA) (Reiter et al., 1998, Proc. Natl. Acad. Sci. USA 95: 1735), and STEAP (Hubert et al., 1999, Proc. Natl. Acad. Sci. USA 96:14523).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

SUMMARY OF THE INVENTION

The present invention relates to methods and compositions for the diagnosis and therapy of prostate cancer. The methods of the invention utilize isolated polynucleotides corresponding to human SGP28, proteins encoded by the SGP28 gene and fragments thereof, and antibodies capable of specifically recognizing and binding to SGP28 proteins. The methods of the invention are based, in part, on the molecular cloning of a gene that is identical to SGP28 and that is highly overexpressed in human prostate cancers. The invention is further based on the discovery that, as determined by immunohistochemistry, very high levels of SGP28 protein are expressed and secreted into the lumen of cancerous prostate glands as well as in PIN, a non-invasive precancerous prostate lesion, and in bone and lymph node metastases. The expression profile of SGP28 disclosed herein indicates that SGP28 provides a useful diagnostic marker and/or therapeutic target for prostate cancer. Moreover, the expression of SGP28 in PIN suggests that it may be a marker for early diagnosis of prostate cancer, a much needed improvement over what is presently available using PSA. The expression pattern of SGP28 in individual clinical specimens suggests that SGP28 can be used to identify individual patients who will be more responsive to one treatment modality versus another. In addition, SGP28 may serve as a surrogate marker for monitoring the efficacy of a prostate cancer therapeutic regimen. SGP28 molecules provide a particularly attractive marker for use in in vivo imaging methods due to its expression in lymph node and bone metastases.

SGP28 mRNA expression is restricted to the prostate and ovary, and is markedly up-regulated in prostate tumors. Expression of SGP28 in matched normal prostate/tumor samples from advanced prostate cancer patients, using both mRNA and protein detection methods, shows a high degree of up-regulated expression in the tumor tissue, suggesting that SGP28 is a useful marker for prostate cancer detection.

SGP28 is an extracellular soluble protein that has a predicted molecular weight of 29 kDa and a pI of 8.08. SGP28 has a signal peptide that is cleaved between amino acid residues 32 and 33, and includes two extracellular protein SCP motifs (prosite domain PDOC00772), one at amino acids 150–160 and another at amino acids 170–182, both of SEQ ID NO: 3. The protein has strong homology to defensin proteins, particularly to beta-defensins, which are secreted products produced mainly by epithelial cells (O-Neil et al., 1999, J. Immunol. 163:6718–24; Schroder et al., 1999, Int. J. Biochem. Cell Biol., 31:645–51). As a defensin, the SGP28 protein may have the ability to induce tumor cell death and/or may serve as a chemoattractant. SGP28 may also have a role in cell binding and/or in inducing cell growth.

A number of potential approaches to the treatment of prostate cancer and other cancers expressing SGP28 are described herein. The extracellular and soluble nature of this protein presents a number of therapeutic approaches using molecules that target SGP28 and its function, as well as molecules that target other proteins, factors and ligands that interact with SGP28. These therapeutic approaches include antibody therapy with anti-SGP28 antibodies, small molecule therapies, and vaccine therapies. In addition, given its up-regulated expression in prostate cancer, SGP28 is useful as a diagnostic, staging and/or prognostic marker for prostate cancer and, similarly, may be a marker for other cancers expressing this protein.

The invention provides polynucleotides corresponding or complementary to all or part of the SGP28 gene as described herein, mRNAs, and/or coding sequences, preferably in isolated form, including polynucleotides encoding SGP28 proteins and fragments thereof, DNA, RNA, DNA/RNA hybrid, and related molecules, polynucleotides or oligonucleotides complementary to the SGP28 gene or mRNA sequences or parts thereof, and polynucleotides or oligonucleotides which hybridize to the SGP28 gene, mRNAs, or to SGP28-encoding polynucleotides. Also provided are means for isolating cDNAs and the genes encoding SGP28. Recombinant DNA molecules containing SGP28 polynucleotides, cells transformed or transduced with such molecules, and host vector systems for the expression of SGP28 gene products are also provided.

The invention further provides SGP28 proteins and polypeptide fragments thereof, as well as antibodies that bind to SGP28 proteins and polypeptide fragments thereof. The antibodies of the invention include polyclonal and monoclonal antibodies, murine and other mammalian antibodies, chimeric antibodies, humanized and fully human antibodies, antibodies labeled with a detectable marker, and antibodies conjugated to radionuclides, toxins or other therapeutic compositions.

The invention further provides methods for detecting the presence of SGP28 polynucleotides and proteins in various biological samples, as well as methods for identifying cells that express SGP28. The invention further provides various therapeutic compositions and strategies, including particularly, antibody, vaccine and small molecule therapy, for treating cancers of the prostate.

BRIEF DESCRIPTION OF THE FIGURES

FIGS. 1A–C. Northern blot analysis of SGP28 mRNA expression in normal tissues (FIGS. 1A and 1B) and high level up-regulated expression in prostate cancer xenografts (Panel C). The lower molecular weight signal in normal testis is probably due to cross-hybridization of the probe (SSH fragment) to CRISP2/TPX-1 message. An identical transcript is seen for CRISP2 on this normal panel using a gene specific oligonucleotide probe as described by Kratzschmar et al., 1996, Eur J Biochem 236(3):827–36. In FIG. 1A, lane 1 is heart, lane 2 is brain, lane 3 is placenta, lane 4 is lung, lane 5 is liver, lane 6 is skeletal muscle, lane 7 is kidney, and lane 8 is pancreas. In FIG. 1B, lane 1 is spleen, lane 2 is thymus, lane 3 is prostate, lane 4 is testis, lane 5 is ovary, lane 6 is small intestine, lane 7 is colon, and lane 8 is leukocytes. In FIG. 1C, lane 1 is prostate, lane 2 is LAPC-4 AD, lane 3 is LAPC-4 AI, lane 4 is LAPC-9 AD, and lane 5 is LAPC-9 AI.

FIG. 8B shows the same at 800×. SGP28 expression in PIN is shown in FIG. 8C at 200×, and in FIG. 8D at 800×.

DETAILED DESCRIPTION OF THE INVENTION

The present invention relates to methods and compositions for the diagnosis and therapy of prostate cancer which utilize isolated polynucleotides corresponding to the human SGP28 gene, proteins encoded by the SGP28 gene and fragments thereof, and antibodies capable of specifically recognizing and binding to SGP28 proteins. The invention is based, in part, upon the isolation of a cDNA fragment corresponding to the SGP28 gene by suppression subtraction hybridization cloning. This cDNA, designated 36P1G3, was sequenced and analyzed for homology to known genes and ESTs in the major public databases. The 36P1 G3 cDNA showed identity to part of the reported sequence of the human SGP28 gene. Primers designed to specifically amplify the gene corresponding to 36P1G3 were then used to characterize SGP28 expression in prostate cancer xenografts, normal prostate, and a variety of other normal tissues. The nucleotide and amino acid sequences of SGP28 have been reported (Kjeldsen et al., 1996, FEBS Lett. 380: 246–250; Kratzschmar et al., 1996, Eur J Biochem 236(3) :827–36).

Figure 2:
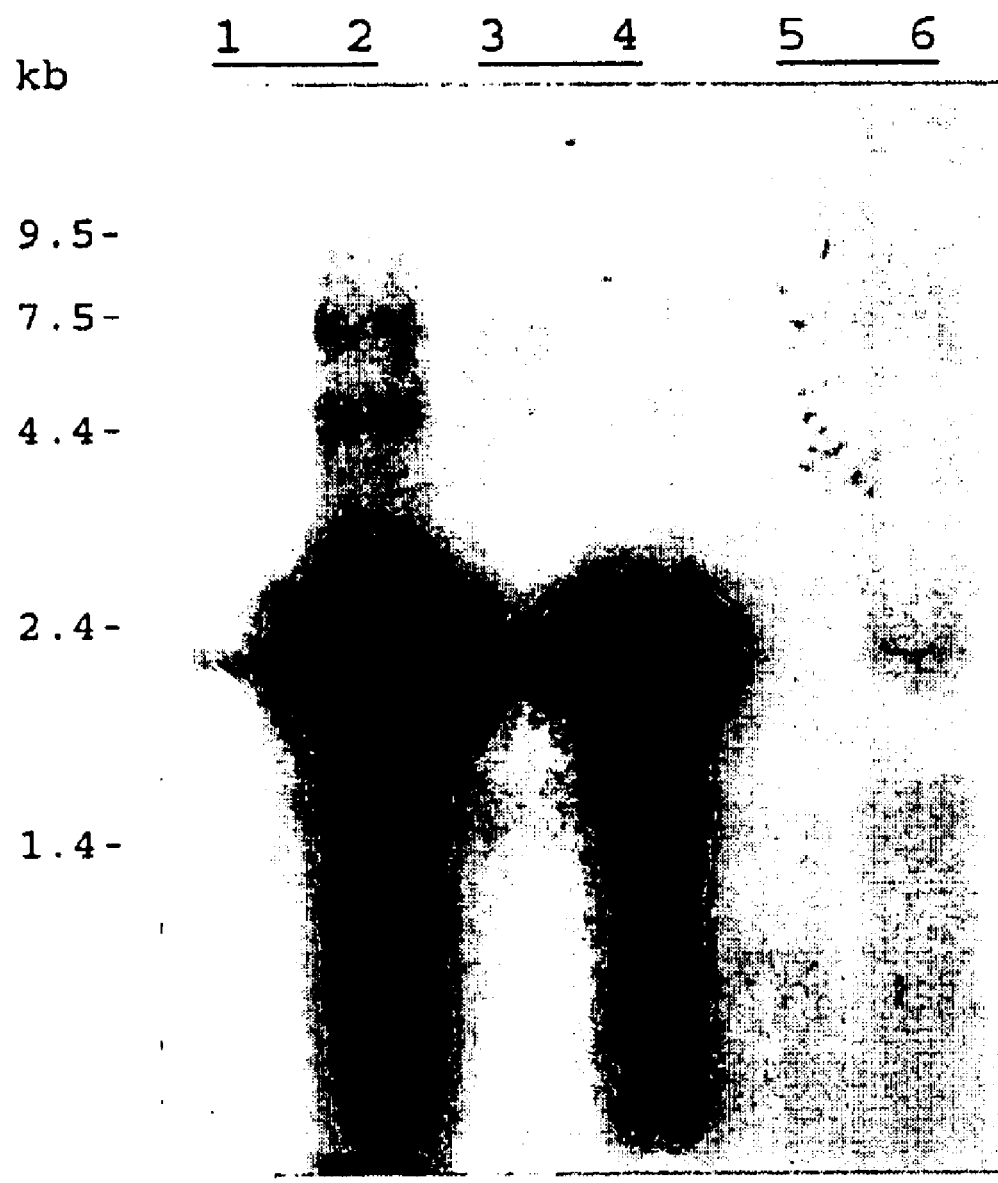
FIG. 2 Northern blot analysis of SGP28/36P1G3 mRNA expression in a panel of 3 prostate tumor (lanes 2, 4, 6) and normal adjacent tissue (lanes 1, 3, 5) pairs, showing upregulation in 3 of the 3 tumor specimens.

The expression profile of SGP28 suggests that it may represent an ideal diagnostic and therapeutic marker for prostate cancer. As determined by northern blot expression analysis, the expression of SGP28 mRNA in normal tissues is highly restricted to prostate, testis and ovary (FIGS. 1A–B). Very low level expression is detectable in pancreas (FIG. 1A). Interestingly, the prostate and ovary exhibit a 2.4 kb transcript, while testis expresses a 1.6 kb message (the 1.6 kb message could represent another SGP28 family member). Further, SGP28 mRNA expression is highly upregulated in prostate cancer xenografts derived from advanced metastatic stage disease (FIG. 1C). In addition, SGP28 protein is expressed at high levels in these same prostate cancer xenografts as well as in prostate cancer clinical specimens (FIG. 2). In matched normal/cancerous prostate cancer clinical specimens, high level overexpression of SGP28 protein relative to normal is detected, indicating that SGP28 provides an excellent diagnostic marker and/or therapeutic target for prostate cancer. Immunohistochemical analysis establishes that SGP28 protein is expressed and secreted at high levels into the lumen of cancerous and precancerous prostate glands, as well as in metastatic disease. Like PSA, SGP28 is secreted into the lumen and enters the serum in tissues where normal architecture is disturbed.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37° C. and temperatures for washing in 0.1×SSC/0.1% SDS are above 55° C., and most preferably to stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example. 50% (v/v) formamide with 0.1% bovine serum albumin/0.1% FICOLL™/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. FICOLL™ is a registered trademark for a synthetic sucrose polymer.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

In the context of amino acid sequence comparisons, the term "identity" is used to express the percentage of amino acid residues at the same relative positions that are the same. Also in this context, the term "homology" is used to express the percentage of amino acid residues at the same relative positions that are either identical or are similar, using the conserved amino acid criteria of BLAST analysis, as is generally understood in the art. For example, % identity values may be generated by WU-BLAST-2 (Altschul et al., Methods in Enzymology, 266: 460–480 (1996). Further details regarding amino acid substitutions, which are considered conservative under such criteria, are provided below.

Additional definitions are provided throughout the subsections that follow.

SGP28 Polynucleotides

One aspect of the invention provides polynucleotides corresponding or complementary to all or part of a SGP28 gene, mRNA, and/or coding sequence, preferably in isolated form, including polynucleotides encoding a SGP28 protein and fragments thereof, DNA, RNA, DNA/RNA hybrid, and related molecules, polynucleotides or oligonucleotides complementary to a SGP28 gene or mRNA sequence or a part thereof, and polynucleotides or oligonucleotides that hybridize to a SGP28 gene, mRNA, or to a SGP28 encoding polynucleotide (collectively, "SGP28 polynucleotides"). As used herein, the SGP28 gene and protein is meant to include the SGP28 genes and proteins specifically described herein and the genes and proteins corresponding to other SGP28 proteins and structurally similar variants of the foregoing. Such other SGP28 proteins and variants will generally have coding sequences that are highly homologous to the SGP28 coding sequence, and preferably will share at least about 50% amino acid identity and at least about 60% amino acid homology (using BLAST criteria), more preferably sharing 70% or greater homology (using BLAST criteria).

One embodiment of a SGP28 polynucleotide is a SGP28 polynucleotide having the sequence shown in Table 1 (SEQ ID NO: 2). A SGP28 polynucleotide may comprise a polynucleotide having the nucleotide sequence of human SGP28 as shown in Table 1 (SEQ ID NO: 2), wherein T can also be U; a polynucleotide that encodes all or part of the SGP28 protein; a sequence complementary to the foregoing; or a polynucleotide fragment of any of the foregoing. Another embodiment comprises a polynucleotide having the sequence as shown in Table 1 (SEQ ID NO: 2), from nucleotide residue number 3 through nucleotide residue number 776, wherein T can also be U.

Another embodiment is a pharmaceutical composition comprising a polynucleotide that encodes a SGP28 polypeptide, wherein the polynucleotide is selected from the group consisting of (a) a polynucleotide having the sequence as shown in Table 1 (SEQ ID NO: 2), wherein T can also be U; (b) a polynucleotide having the sequence as shown in Table 1 (SEQ ID NO: 2), from nucleotide residue number 3 through nucleotide residue number 776, wherein T can also be U; (c) a polynucleotide encoding a SGP28 protein having the amino acid sequence shown in Table 2 (SEQ ID NO: 3); (d) a polynucleotide that is a fragment of the polynucleotide of (a), (b) or (c) that is at least 20 nucleotide bases in length; (e) a polynucleotide that is fully complementary to a polynucleotide of any one of (a)–(d); or (f) a polynucleotide that selectively hybridizes under stringent conditions to the polynucleotide of any one of (a)–(d).

Typical embodiments of the invention disclosed herein include SGP28 polynucleotides encoding specific portions of the SGP28 mRNA sequence such as those that encode the protein and fragments thereof. For example, representative embodiments of the invention disclosed herein include: polynucleotides encoding about amino acid 1 to about amino acid 10 of the SGP28 protein shown in Table 2 (SEQ ID NO: 3), polynucleotides encoding about amino acid 20 to about amino acid 30 of the SGP28 protein shown in Table 2 (SEQ ID NO: 3), polynucleotides encoding about amino acid 30 to about amino acid 40 of the SGP28 protein shown in Table 2 (SEQ ID NO: 3), polynucleotides encoding about amino acid 40 to about amino acid 50 of the SGP28 protein shown in Table 2 (SEQ ID NO: 3), polynucleotides encoding about amino acid 50 to about amino acid 60 of the SGP28 protein shown in Table 2 (SEQ ID NO: 3), polynucleotides encoding about amino acid 60 to about amino acid 70 of the SGP28 protein shown in Table 2 (SEQ ID NO: 3), polynucleotides encoding about amino acid 70 to about amino acid 80 of the SGP28 protein shown in Table 2 (SEQ ID NO: 3), polynucleotides encoding about amino acid 80 to about amino acid 90 of the SGP28 protein shown in Table 2 (SEQ ID NO: 3) and polynucleotides encoding about amino acid 90 to about amino acid 100 of the SGP28 protein shown in Table 2 (SEQ ID NO: 3), etc. Following this scheme, polynucleotides (of at least 10 amino acids) encoding portions of the amino acid sequence of amino acids 100–258 of the SGP28 protein shown in Table 2 (SEQ ID NO: 3) are typical embodiments of the invention. Polynucleotides encoding larger portions of the SGP28 protein are also contemplated. For example polynucleotides encoding from about amino acid 1 (or 20 or 30 or 40 etc.) to about amino acid 20, (or 30, or 40 or 50 etc.) of the SGP28 protein shown in Table 2 (SEQ ID NO: 3) may be generated by a variety of techniques well known in the art.

Additional illustrative embodiments of the invention disclosed herein include SGP28 polynucleotide fragments encoding one or more of the biological motifs contained within the SGP28 protein sequence. In one embodiment, typical polynucleotide fragments of the invention can encode one or more of the regions of SGP28 that exhibit homology to beta-defensins. In another embodiment of the invention, typical polynucleotide fragments can encode one or more extracellular proteins SCP/Tpx-1/Ag5/PR-1/Sc7 signature sequences. In yet another embodiment of the invention, typical polynucleotide fragments can encode sequences that are unique to one or more SGP28 alternative splicing variants.

The polynucleotides of the preceding paragraphs have a number of different specific uses. As SGP28 is shown to be overexpressed in prostate cancer, these polynucleotides may be used in methods assessing the status of SGP28 gene products in normal versus cancerous tissues. Typically, polynucleotides encoding specific regions of the SGP28 protein may be used to assess the presence of perturbations (such as deletions, insertions, point mutations etc.) in specific regions of the SGP28 gene products. Exemplary assays include both RT-PCR assays as well as single-strand conformation polymorphism (SSCP) analysis (see e.g. Marrogi et al., J. Cutan. Pathol. 26(8): 369–378 (1999), both of which utilize polynucleotides encoding specific regions of a protein to examine these regions within the protein. Assays and methods for analyzing sequences to detect single nucleotide polymorphisms are also available (Irizarry, et al., 2000, Nature Genetics 26(2):223–236.

Other specifically contemplated embodiments of the invention disclosed herein are genomic DNA, cDNAs, ribozymes, and antisense molecules, including morpholino anti-sense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the SGP28 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., SGP28. See for example, Jack Cohen, OLIGODEOXYNUCLEOTIDES, Antisense Inhibitors of Gene Expression, CRC Press, 1989; and Synthesis 1:1–5 (1988). The SGP28 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide, which is a sulfur transfer reagent. See Iyer, R. P. et al, J. Org. Chem. 55:4693–4698 (1990); and Iyer, R. P. et al., J. Am. Chem. Soc. 112:1253–1254 (1990), the disclosures of which are fully incorporated by reference herein. Additional SGP28 antisense oligonucleotides of the present invention include morpholino antisense oligonucleotides known in the art (see e.g. Partridge et al., 1996, Antisense & Nucleic Acid Drug Development 6: 169–175).

The SGP28 antisense oligonucleotides of the present invention typically may be RNA or DNA that is complementary to and stably hybridizes with the first 100 N-terminal codons or last 100 C-terminal codons, or overlapping with the ATG start site, of the SGP28 genome or the corresponding mRNA. While absolute complementarity is not required, high degrees of complementarity are preferred. Use of an oligonucleotide complementary to this region allows for the selective hybridization to SGP28 mRNA and not to mRNA specifying other regulatory subunits of protein kinase. Preferably, the SGP28 antisense oligonucleotides of the present invention are a 15 to 30-mer fragment of the antisense DNA molecule having a sequence that hybridizes to SGP28 mRNA. Optionally, SGP28 antisense oligonucleotide is a 30-mer oligonucleotide that is complementary to a region in the first 10 N-terminal codons and last 10 C-terminal codons of SGP28. Alternatively, the antisense molecules are modified to employ ribozymes in the inhibition of SGP28 expression. L. A. Couture & D. T. Stinchcomb; *Trends Genet* 12: 510–515 (1996).

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a SGP28 polynucleotide in a sample and as a means for detecting a cell expressing a SGP28 protein.

Examples of such probes include polypeptides comprising au or part of the human SGP28 cDNA sequence shown in Table 1 (SEQ ID NO: 2). Examples of primer pairs capable of specifically amplifying SGP28 mRNAs are also described in the Examples that follow. An example of a primer pairs capable of specifically amplifying SGP28 mRNAs is:

5'-AGT TGC CTT TCC TAG CTC CAC TCT-3' (SEQ ID NO: 4)

5'-TCC CTT TCC ATA CTC CAC TCT TTG-3' (SEQ ID NO: 5)

As will be understood by the skilled artisan, a great many different primers and probes may be prepared based on the sequences provided in herein and used effectively to amplify and/or detect a SGP28 mRNA.

As used herein, a polynucleotide is said to be "isolated" when it is substantially separated from contaminant polynucleotides that correspond or are complementary to genes other than the SGP28 gene or that encode polypeptides other than SGP28 gene product or fragments thereof A skilled artisan can readily employ nucleic acid isolation procedures to obtain an isolated SGP28 polynucleotide.

The SGP28 polynucleotides of the invention are useful for a variety of purposes, including but not limited to their use as probes and primers for the amplification and/or detection of the SGP28 gene(s), mRNA(s), or fragments thereof; as reagents for the diagnosis and/or prognosis of prostate cancer and other cancers; as tools for identifying molecules that inhibit calcium entry specifically into prostate cells; as coding sequences capable of directing the expression of SGP28 polypeptides; as tools for modulating or inhibiting the expression of the SGP28 gene(s) and/or translation of the SGP28 transcript(s); and as therapeutic agents.

Molecular and Biochemical Features of SGP28

Specific granule protein 28 (SGP28) is a secreted molecule identified from and expressed in specific granules of human neutrophils (Kjeldsen et al., 1996, FEBS Lett. 380: 246–250). SGP28 is identical to the protein known as Cysteine-rich secretory protein 3 (CRISP-3) (Kratzschmar et al., 1996, Eur. J. Biochem. 236:827–36). SGP28/CRISP-3 (hereinafter referred to as SGP28) is a 29 kD protein of 258 amino acids containing a C-terminal cysteine rich sequence comprising 16 cysteine residues conserved among several CRISP family member proteins. SGP28 belongs to a family of cysteine rich secretory proteins present in humans, rodents, and equine, comprising CRISP-1 (Brooks et al., 1986, Eur. J. Biochem. 161:13–18; Haendler et al., 1993, Endocrinology 133:192–198; Kratzschmar et al., 1996, Eur. J. Biochem. 236:827–36), CRISP-2/TPX-1 (Kasahara et al., 1989, Genomics 5:527–534; Mizuki et al., 1992, Mamm. Genome 3:274–280) and CRISP-3/SGP28 (Haendler et al., 1993, Endocrinology 133:192–198; Schambony et al., 1998. Biochimica et Biophysica Acta 1387:206–216; Schwidetzky et al., 1995, Biochem. J. 309:831–836).

Human SGP28 has been identified in granules of neutrophils and SGP28 expression has been detected in salivary gland, pancreas, prostate, epididymis, ovary and colon (Kratzschmar et al., 1996, Eur. J. Biochem. 236:827–36). Expression of murine CRISP family proteins have been detected in B-cells, salivary and lacrimal glands, epididymis, testis and mucosal cells (Pfisterer et al., 1996, Mol. Cell. Biol. 16:6160–6168; Haendler et al., 1999 J. Cell. Physiology 178:371–378, Haendler et al., 1997, Eur. J. Biochem. 250:440–446), and murine CRISP-2 and CRISP-3 are androgen regulated (Haendler et al., 1999 J. Cell. Physiology 178:371–378, Haendler et al., 1997, Eur. J. Biochem. 250:440–446). It has been suggested that SGP28 and other CRISP family members may have a role in non-specific innate immunity (Kjeldsen et al., 1996, FEBS Lett. 380: 246–250; Pfisterer et al., 1996, Mol. Cell. Biol. 16:6160–6168, Haendler et al., 1999 J. Cell Physiology 178:371–378).

As is described further in the Examples that follow, the SGP28 gene and protein have been characterized in a variety of ways. For example, analyses of nucleotide coding and amino acid sequences were conducted in order to identify conserved structural elements within the SGP28 sequence, topological features, post-translational modifications, and potentially related molecules. Northern blot analyses of SGP28 mRNA expression were conducted in order to establish the range of normal and cancerous tissues expressing the various SGP28 messages. Western blot and immunohistochemical analyses of SGP28 protein expression in experimentally transfected and cancerous cells and tissues were conducted to determine expression and secretion patterns. SGP28 has a pI of 8.08 and a calculated molecular weight of 29.0 kDa.

Several secreted proteins have been described in prostate cancer, a number of which have been shown to participate in the process of tumor formation and progression (Inoue K., 2000; Clin. Cancer Res. 6:2104–19; Dow J K et al., 2000, Urology 55:800–6). As SGP28 is a secreted protein, one of its potential functions is to regulate the microenvironment of prostate cancer and of metastatic disease. In order to test this possibility, SGP28 can be expressed and purified as a recombinant GST-SGP28 or SGP28-Myc/His form. Purified recombinant-SGP28 (such as GST-SGP28 or SGP28-Myc/His) is then incubated with a variety of cell types that recapitulate the environment of the prostate, including prostate epithelial cells, prostate tumor cell lines, prostate stromal cells, prostate endothelial cells and prostate neuroendocrine cells. In addition, recombinant-SGP28 is also incubated with cells found at metastatic sites, such as bone marrow cells and cells of the immune system. Binding of SGP28 to intact cells is detected by FACS analysis and by calorimetric assay. This analysis is valuable as it identifies a cell population that binds and may respond to SGP28. In addition, the identification of a target cell population may provide a means of isolating and identifying SGP28 receptors.

SGP28 has a strong homology to defensin proteins, in particular to β-defensins. Beta-defensins are secreted products mainly produced by epithelial cells (O'Neil D A et al, 1999, J. Immunol. 163:6718–24; Schroder J M, Harder J., 1999, Int. J. Biochem. Cell Biol. 31:645–51). Defensins play an important role in preventing infections and safeguarding the immunity of epithelial tissues. In addition, the human HNP1 defensin has been shown to induce the death of tumor cells in vitro. Investigating the role of SGP28 in cell death, purified recombinant-SGP28 is incubated with a variety of cell types listed above and analyzed for apoptotic activity using FACS analysis of Annexin V stained cells. SGP28 may also function as a chemoattractant, as has been shown for other defensin molecules (Yang D et al. Leukoc Biol. 2000;68:9–14, Yang D et al. Science. 1999, 286(5439):525–8.). Using a chemotactic assay, one can evaluate the effect of SGP28 on the migration of various types of cells, including epithelial, stromal, endothelial cells as well as monocytes, lymphocytes and dendritic cells.

Isolation of SGP28-Encoding Nucleic Acid Molecules

The SGP28 cDNA sequences described herein enable the isolation of other polynucleotides encoding SGP28 gene product(s), as well as the isolation of polynucleotides encoding SGP28 gene product homologues, alternatively spliced isoforms, allelic variants, and mutant forms of the SGP28 gene product. Various molecular cloning methods that can be employed to isolate full length cDNAs encoding a SGP28 gene are well known (See, for example, Sambrook, J. et al. Molecular Cloning: A Laboratory Manual, 2d edition., Cold Spring Harbor Press, New York, 1989; Current Protocols in Molecular Biology. Ausubel et al., Eds., Wiley and Sons, 995). For example, lambda phage cloning methodologies may be conveniently employed, using commercially available cloning systems (e.g. Lambda ZAP Express™, which are DNA vector kits consisting essentially of vectors and reagents sold by STRATAGENE™). Phage clones containing SGP28 gene cDNAs may be identified by probing with labeled SGP28 cDNA or a fragment thereof. For example, in one embodiment, the SGP28 cDNA (Table 1; SEQ ID NO: 2) or a portion thereof can be synthesized and used as a probe to retrieve overlapping and full length cDNAs corresponding to a SGP28 gene. The SGP28 gene itself may be isolated by screening genomic DNA libraries, bacterial artificial chromosome libraries (BACs), yeast artificial chromosome libraries (YACs), and the like, with SGP28 DNA probes or primers.

Recombinant DNA Molecules and Host-Vector Systems

The invention also provides recombinant DNA or RNA molecules containing a SGP28 polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The invention further provides a host-vector system comprising a recombinant DNA molecule containing a SGP28 polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 cell). Examples of suitable mammalian cells include various prostate cancer cell lines such LNCaP, PC-3, DU145, LAPC-4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a SGP28 may be used to generate SGP28 proteins or fragments thereof using any number of host vector systems routinely used and widely known in the art.

A wide range of host vector systems suitable for the expression of SGP28 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (INVITROGEN™) and the retroviral vector pSRαtkneo (Muller et al., 1991, MCB 11: 1785). Using these expression vectors, SGP28 may be preferably expressed in several prostate cancer and non-prostate cell lines, including for example 293, 293T, rat-1, 3T3, PC-3, LNCaP and TsuPr1. The host vector systems of the invention are useful for the production of a SGP28 protein or fragment thereof. Such host-vector systems may be employed to study the functional properties of SGP28 and SGP28 mutations.

Proteins encoded by the SGP28 genes, or by fragments thereof, will have a variety of uses, including but not limited to generating antibodies and in methods for identifying ligands and other agents and cellular constituents that bind to a SGP28 gene product. Antibodies raised against a SGP28 protein or fragment thereof may be useful in diagnostic and prognostic assays, imaging methodologies (including, particularly, cancer imaging), and therapeutic methods in the management of human cancers characterized by expression of a SGP28 protein, including but not limited to cancer of the prostate. Various immunological assays useful for the detection of SGP28 proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting prostate cells (e.g., in radioscintigraphic imaging methods). SGP28 proteins may also be particularly useful in generating cancer vaccines, as further described below.

SGP28 Proteins

Another aspect of the present invention provides SGP28 proteins and polypeptide 23 fragments thereof. The SGP28 proteins of the invention include those specifically identified herein, as well as allelic variants, conservative substitution variants and homologs to the extent that such variants and homologs can be isolated/generated and characterized without undue experimentation following the methods outlined below. Fusion proteins that combine parts of different SGP28 proteins or fragments thereof, as well as fusion proteins of a SGP28 protein and a heterologous polypeptide, are also included. Such SGP28 proteins will be collectively referred to as the SGP28 proteins, the proteins of the invention, or SGP28. As used herein, the term "SGP28 polypeptide" refers to a polypeptide fragment or a SGP28 protein of at least 10 amino acids, preferably at least 15 amino acids.

A specific embodiment of a SGP28 protein comprises a polypeptide having the amino acid sequence of human SGP28 as shown in Table 2 (SEQ ID NO: 3), from amino acid residue number 1 through about amino acid residue number 258 as shown therein. Another specific embodiment of a SGP28 protein comprises a polypeptide having the amino acid sequence of human SGP28 as shown in Table 2 (SEQ ID NO: 3), from about amino acid residue number 33 through about amino acid residue number 258 as shown therein. A specific embodiment of a SGP28 fragment comprises a peptide selected from the group comprising amino acids 1–32 of the SGP28 protein sequence shown in Table 2 (SEQ ID NO: 3), or one or both of the extracellular protein SCP motifs at amino acid residues 150–160 (VVGHYTQVVWY; SEQ ID NO: 6) and 170–182 (YYVCQYCPAGNW; SEQ ID NO:7).

In general, naturally occurring allelic variants of human SGP28 will share a high degree of structural identity and homology (e.g., 90% or more identity). Typically, allelic variants of the SGP28 proteins will contain conservative amino acid substitutions within the SGP28 sequences described herein or will contain a substitution of an amino acid from a corresponding position in a SGP28 homologue. One class of SGP28 allelic variants will be proteins that share a high degree of homology with at least a small region of a particular SGP28 amino acid sequence, but will further contain a radical departure from the sequence, such as a non-conservative substitution, truncation insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D)) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently b interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

SGP28 proteins, including variants, comprise at least one epitope in common with a SGP28 protein having the amino acid sequence of Table 2 (SEQ ID NO: 3), such that an antibody that specifically binds to a SGP28 protein or variant will also specifically bind to the SGP28 protein having the amino acid sequence of Table 2 (SEQ ID NO: 3). One class of SGP28 protein variants shares 90% or more identity with the amino acid sequence of Table 2 (SEQ ID NO: 3). A more specific class of SGP28 protein variants comprises an extracellular protein SCP motif as described above. Preferred SGP28 protein variants are capable of exhibiting one or more of the defensin functions described herein, including, for example, the ability to induce tumor death or to chemoattract and/or induce migration of cells.

SGP28 proteins may be embodied in many forms, preferably in isolated form. As used herein, a protein is said to be "isolated" when physical, mechanical or chemical methods are employed to remove the SGP28 protein from cellular constituents that are normally associated with the protein. A skilled artisan can readily employ standard purification methods to obtain an isolated SGP28 protein. A purified SGP28 protein molecule will be substantially free of other proteins or molecules that impair the binding of SGP28 to antibody or other ligand. The nature and degree of isolation and purification will depend on the intended use. Embodiments of a SGP28 protein include a purified SGP28 protein and a functional, soluble SGP28 protein. In one form, such functional, soluble SGP28 proteins or fragments thereof retain the ability to bind antibody or other ligand.

The invention also provides SGP28 polypeptides comprising biologically active fragments of the SGP28 amino acid sequence, such as a polypeptide corresponding to part of the amino acid sequence for SGP28 as shown in Table 2 (SEQ ID NO: 3). Such polypeptides of the invention exhibit properties of the SGP28 protein, such as the ability to elicit the generation of antibodies that specifically bind an epitope associated with the SGP28 protein.

Embodiments of the invention disclosed herein include a wide variety of art accepted variants of SGP28 proteins such as polypeptides having amino acid insertions, deletions and substitutions. SGP28 variants can be made using methods known in the art such as site-directed mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., Gene, 34:315 (1985)], restriction selection mutagenesis [Wells et al., *Philos. Trans. R. Soc. London SerA*, 317:415 (1986)] or other known techniques can be performed on the cloned DNA to produce the SGP28 variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, J. Mol. Biol., 150:1 (1976)]. If alanine substitution does not yield adequate amounts of variant, an isosteric amino acid can be used.

As discussed above, embodiments of the claimed invention include polypeptides containing less than the 258 amino acid sequence of the SGP28 protein shown in Table 2 (SEQ ID NO: 3). For example, representative embodiments of the invention disclosed herein include polypeptides consisting of about amino acid 1 to about amino acid 10 of the SGP28 protein shown in Table 2 (SEQ ID NO: 3), polypeptides consisting of about amino acid 20 to about amino acid 30 of the SGP28 protein shown in Table 2 (SEQ ID NO: 3), polypeptides consisting of about amino acid 30 to about amino acid 40 of the SGP28 protein shown in Table 2 (SEQ ID NO: 3), polypeptides consisting of about amino acid 40 to about amino acid 50 of the SGP28 protein shown in Table 2 (SEQ ID NO: 3), polypeptides consisting of about amino acid 50 to about amino acid 60 of the SGP28 protein shown in Table 2 (SEQ ID NO: 3), polypeptides consisting of about amino acid 60 to about amino acid 70 of the SGP28 protein shown in Table 2 (SEQ ID NO: 3), polypeptides consisting of about amino acid 70 to about amino acid 80 of the SGP28 protein shown in Table 2 (SEQ ID NO: 3), polypeptides consisting of about amino acid 80 to about amino acid 90 of the SGP28 protein shown in Table 2 (SEQ ID NO: 3) and polypeptides consisting of about amino acid 90 to about amino acid 100 of the SGP28 protein shown in Table 2 (SEQ ID NO: 3), etc. Following this scheme, polypeptides consisting of portions of the amino acid sequence of amino acids 100–258 of the SGP28 protein are typical embodiments of the invention. Polypeptides consisting of larger portions of the SGP28 protein are also contemplated. For example polypeptides consisting of about amino acid 1 (or 20 or 30 or 40 etc.) to about amino acid 20, (or 30, or 40 or 50 etc.) of the SGP28 protein shown in Table 2 (SEQ ID NO: 3) may be generated by a variety of techniques well known in the art.

Additional illustrative embodiments of the invention disclosed herein include SGP28 polypeptides containing the amino acid residues of one or more of the biological motifs contained within the SGP28 polypeptide sequence as shown in Table 2 (SEQ ID NO: 3). SGP28 polypeptides containing one or more of these motifs or other select regions of interest described herein will typically include an additional 5 to 25 or more amino acid residues of adjacent SGP28 protein sequence on one or both sides of the selected motif(s). In one embodiment, typical polypeptides of the invention can contain one or more of the regions of SGP28 that exhibit homology to defensins. In another embodiment, typical polypeptides of the invention can contain one or more of the SGP28 N-glycosylation sites such as NCSN (SEQ ID NO: 8) at residues 252–255 (numbering from first amino acid Fag residue shown in SEQ ID NO: 3). In another embodiment, typical polypeptides of the invention can contain one or more of the SGP28 protein kinase C phosphorylation sites such as SLK at residues 106–108 and/or 231–233. In another embodiment, typical polypeptides of the invention can contain one or more of the SGP28 casein kinase II phosphorylation sites such as SWFD at residues 128–131 (SEQ ID NO: 9) and/or SCPD at residues 206–209 (SEQ ID NO: 10). In another embodiment, typical polypeptides of the invention can contain one or more of the tyrosine kinase phosphorylation sites such as KCGENLY at residues 108–114 (SEQ ID NO: 11). In another embodiment, typical polypeptides of the invention can contain one or more of the N-myristoylation sites such as GLLPSF at residues 26–31 (SEQ ID NO: 12), GCGNAY at residues 164–169 (SEQ ID NO: 13), GNWANR at residues 188–193 (SEQ ID NO: 14), GAPCAS at residues 201–206 (SEQ ID NO: 15) and/or GLCTNG at residues 214–219 (SEQ ID NO: 16). In another embodiment, typical polypeptides of the invention can contain one or more of the extracellular protein SCP signature sequences, such as amino acid residues 150–160 of SEQ ID NO: 3, and/or amino acid residues 179–190 of SEQ ID NO: 3. In another embodiment, typical polypeptides of the invention can contain one or more predicted HLA-A2 binding peptides such as amino acids 2–10 (TLFPVLLFL; SEQ ID NO: 17), amino acids 6–14 (VLLFLVAGL; SEQ ID NO: 18), amino acids 30–38 (ALLTTQTQV; SEQ ID NO: 19), amino acids 142–150 (VVWYSSYLV; SEQ ID NO: 20), amino acids 222–230 (TLTCKHQLV; SEQ ID NO: 21), amino acids 175–183 (GNWANRLYV; SEQ ID NO: 22), amino acids 7–15 (LLFLVAGLL; SEQ ID NO: 23), amino acids 141–149 (QVVWYSSYL; SEQ ID NO: 24), amino acids 134–142 (AVVGHYTQV; SEQ ID NO: 25), and amino acids 211–219 (DLYSNCKSL; SEQ ID NO: 26) of SGP28. Related embodiments of these inventions include polypeptides containing combinations of the different motifs discussed above with preferable embodiments being those that contain no insertions, deletions or substitutions either within the motifs or the intervening sequences of these polypeptides.

SGP28 polypeptides can be generated using standard peptide synthesis technology or using chemical cleavage methods well known in the art based on the amino acid sequences of the human SGP28 proteins disclosed herein. Alternatively, recombinant methods can be used to generate nucleic acid molecules that encode a polypeptide fragment of a SGP28 protein. In this regard, the SGP28-encoding nucleic acid molecules described herein provide means for generating defined fragments of SGP28 proteins. SGP28 polypeptides are particularly useful in generating and characterizing domain specific antibodies (e.g., antibodies recognizing an extracellular or intracellular epitope of a SGP28 protein), in identifying agents or cellular factors that bind to SGP28 or a particular structural domain thereof, and in various therapeutic contexts, including but not limited to cancer vaccines. SGP28 polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-SGP28 antibodies or in identifying cellular factors that bind to SGP28.

In a specific embodiment described in the examples that follow, a secreted form of SGP28 may be conveniently expressed in 293T cells transfected with a CMV-driven expression vector encoding SGP28 with a C-terminal 6×His and MYC tag (pcDNA3.1/mycHIS, INVITROGEN™). The secreted HIS-tagged SGP28 in the culture media may be purified using a nickel column and standard techniques. Alternatively, an AP-tag system may be used. Various constructs for expression of SGP28 are described in the examples below.

Modifications of SGP28 such as covalent modifications are included within the scope of this invention. One type of covalent modification includes reacting targeted amino acid residues of an SGP28 polypeptide with an organic derivatizing agent that is capable of reacting with selected side chains or the N- or C-terminal residues of the SGP28. Another type of covalent modification of the SGP28 polypeptide included within the scope of this invention comprises altering the native glycosylation pattern of the polypeptide. "Altering the native glycosylation pattern" is intended for purposes herein to mean deleting one or more carbohydrate moieties found in native sequence SGP28 (either by removing the underlying glycosylation site or by deleting the glycosylation by chemical and/or enzymatic means), and/or adding one or more glycosylation sites that are not present in the native sequence SGP28. In addition, the phrase includes qualitative changes in the glycosylation of the native proteins, involving a change in the nature and proportions of the various carbohydrate moieties present. Another type of covalent modification of SGP28 comprises linking the SGP28 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The SGP28 of the present invention may also be modified in a way to form a chimeric molecule comprising SGP28 fused to another, heterologous polypeptide or amino acid sequence. In one embodiment, such a chimeric molecule comprises a fusion of the SGP28 with a polyhistidine epitope tag, which provides an epitope to which immobilized nickel can selectively bind. The epitope tag is generally placed at the amino- or carboxyl-terminus of the SGP28. In an alternative embodiment, the chimeric molecule may comprise a fusion of the SGP28 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an SGP28 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

SGP28 Antibodies

Another aspect of the invention provides antibodies that bind to SGP28 proteins and polypeptides. The most preferred antibodies will selectively bind to a SGP28 protein and will not bind (or will bind weakly) to non-SGP28 proteins and polypeptides. Anti-SGP28 antibodies that are particularly contemplated include monoclonal and polyclonal antibodies as well as fragments containing the antigen-binding domain and/or one or more complementarity determining regions of these antibodies. As used herein, an antibody fragment is defined as at least a portion of the variable region of the immunoglobulin molecule that binds to its target, i.e., the antigen binding region.

For some applications, it may be desirable to generate antibodies that specifically react with a particular SGP28 protein and/or an epitope within a particular structural domain. For example, preferred antibodies useful for cancer therapy and diagnostic imaging purposes are those which react with an epitope in an extracellular region of the SGP28 protein as expressed in cancer cells. Such antibodies may be generated by using the SGP28 proteins described herein, or using peptides derived from predicted extracellular domains thereof, as an immunogen. In this regard, with reference to the SGP28 protein sequence shown in FIG. 1, regions in the sequence amino-terminal to the transmembrane domain may be selected and used to design appropriate immunogens and screening reagents for raising and selecting extracellular-specific SGP28 antibodies.

SGP28 antibodies of the invention may be particularly useful in prostate cancer therapeutic strategies, diagnostic and prognostic assays, and imaging methodologies. Similarly, such antibodies may be useful in the treatment, diagnosis, and/or prognosis of other cancers, to the extent SGP28 is also expressed or overexpressed in other types of cancer. The invention provides various immunological assays useful for the detection and quantification of SGP28 and mutant SGP28 proteins and polypeptides. Such assays generally comprise one or more SGP28 antibodies capable of recognizing and binding a SGP28 or mutant SGP28 protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer are also provided by the invention, including but limited to radioscintigraphic imaging methods using labeled SGP28 antibodies. Such assays may be used clinically in the detection, monitoring, and prognosis of prostate cancer, particularly advanced prostate cancer.

SGP28 antibodies may also be used in methods for purifying SGP28 and mutant SGP28 proteins and polypeptides and for isolating SGP28 homologues and related molecules. For example, in one embodiment, the method of purifying a SGP28 protein comprises incubating a SGP28 antibody, which has been coupled to a solid matrix, with a lysate or other solution containing SGP28 under conditions which permit the SGP28 antibody to bind to SGP28; washing the solid matrix to eliminate impurities; and eluting the SGP28 from the coupled antibody. Other uses of the SGP28 antibodies of the invention include generating anti-idiotypic antibodies that mimic the SGP28 protein.

SGP28 antibodies may also be used therapeutically by, for example, modulating or inhibiting the biological activity of a SGP28 protein or targeting and destroying cancer cells expressing a SGP28 protein. Antibody therapy of prostate and other cancers is more specifically described in a separate subsection below.

Various methods for the preparation of antibodies are well known in the art. For example, antibodies may be prepared by immunizing a suitable mammalian host using a SGP28 protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). Examples of protein immunogens include recombinant SGP28 (expressed in a baculovirus system, mammalian system, etc.), SGP28 extracellular domain, AP-tagged SGP28, etc. In addition, fusion proteins of SGP28 may also be used, such as a fusion of SGP28 with GST, maltose-binding protein (MBP), green fluorescent protein (GFP), HisMax-TOPO or MycHis (see Examples below).

In a particular embodiment, a GST fusion protein comprising all or most of the open reading frame amino acid sequence of Table 2 (SEQ ID NO: 3) may be produced and used as an immunogen to generate appropriate antibodies. Cells expressing or overexpressing SGP28 may also be used for immunizations. Similarly, any cell engineered to express SGP28 may be used. Such strategies may result in the production of monoclonal antibodies with enhanced capacities for recognizing endogenous SGP28. Another useful immunogen comprises SGP28 peptides linked to the plasma membrane of sheep red blood cells.

The amino acid sequence of SGP28 as shown in Table 2 (SEQ ID NO: 3) may be used to select specific regions of the SGP28 protein for generating antibodies. For example, hydrophobicity and hydrophilicity analyses of the SGP28 amino acid sequence may be used to identify hydrophilic regions in the SGP28 structure. Regions of the SGP28 protein that show immunogenic structure, as well as other regions and domains, can readily be identified using various other methods known in the art, such as Chou-Fasman, Garnier Robson, Kyte-Doolittle, Eisenberg, Karplus-Schultz or Jameson-Wolf analysis. Peptides of SGP28 predicted to bind HLA-A2 may be selected for the generation of antibodies. Such predicted HLA-A2 binding peptides include, but are not limited to, amino acids 2–10 (TLFPVLLFL; SEQ ID NO: 17), amino acids 6–14 (VLLFLVAGL; SEQ ID NO: 18), amino acids 30–38 (ALLTTQTQV; SEQ ID NO: 19), amino acids 142–150 (VVWYSSYLV; SEQ ID NO: 20), amino acids 222–230 (TLTCKHQLV; SEQ ID NO: 21), amino acids 175–183 (GNWANRLYV; SEQ ID NO: 22), amino acids 7–15 (LLFLVAGLL; SEQ ID NO: 23), amino acids 141–149 (QVVWYSSYL; SEQ ID NO: 24), amino acids 134–142 (AVVGHYTQV; SEQ ID NO: 25), and amino acids 211–219 (DLYSNCKSL; SEQ ID NO: 26) of SGP28. As discussed in the examples below, immunogenicity has been demonstrated with SGP28, which was used to generate polyclonal and monoclonal antibodies using rabbits and mice, respectively. This B cell response (antibody production) is the result of an initial T cell response elicited by the immunogenic portions of SGP28.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a SGP28 immunogen is conducted generally by injection over a suitable period and with use of a suitable adjuvant, as is generally understood in the art. During the immunization schedule, titers of antibodies can be taken to determine adequacy of antibody formation.

SGP28 monoclonal antibodies are preferred and may be produced by various means well known in the art. For example, immortalized cell lines which secrete a desired monoclonal antibody may be prepared using the standard hybridoma technology of Kohler and Midstein or modifications which immortalize producing B cells, a is generally known. The immortalized cell lines secreting the desired antibodies are screened by immunoassay in which the antigen is the SGP28 protein or SGP28 fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the SGP28 protein can also be produced in the context of chimeric or CDR grafted antibodies of multiple species origin. Humanized or human SGP28 antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522–525; Riechmann et al., 1988, Nature 332: 323–327; Verhoeyen et al., 1988, Science 239:1534–1536). See also, Carter et al., 1993, Proc. Nat'l Acad. Sci. USA 89: 4285 and Sims et al., 1993, J. Immunol. 151: 2296. Methods for producing fully human monoclonal antibodies include phage display and transgenic animal technologies (for review, see Vaughan et al., 1998, Nature Biotechnology 16: 535–539).

Fully human SGP28 monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45–64 (1993); Burton and Barbas, Human Antibodies from combinatorial libraries. Id., pp 65–82). Fully human SGP28 monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607–614). This method avoids the in vitro manipulation required with phage display technology and efficiently produces high affinity authentic human antibodies.

Reactivity of SGP28 antibodies with a SGP28 protein may be established by a number of well known means, including western blot, immunoprecipitation, ELISA, and FACS analyses using, as appropriate, SGP28 proteins, peptides, SGP28 expressing cells or extracts thereof.

A SGP28 antibody or fragment thereof of the invention may be labeled with a detectable marker or conjugated to a second molecule, such as a cytotoxin or other therapeutic agent, and used for targeting the second molecule to a SGP28 positive cell (Vitetta, E. S. et al., 1993, Immunotoxin therapy, in DeVita, Jr., V. T. et al., eds., Cancer: Principles and Practice of Oncology, 4th ed., J.B. Lippincott Co., Philadelphia, 2624–2636). Examples of cytotoxic agents include, but are not limited to ricin, ricin A-chain, doxorubicin, daunorubicin, TAXOL™ (an anticancer preparation), ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, saponaria officinalis inhibitor, and glucocorticoid and other chemotherapeutic agents, as well as radioisotopes such as $^{212}$Bi, $^{131}$I, $^{131}$In, $^{90}$Y and $^{186}$Re. Suitable detectable markers include, but are not limited to, a radioisotope, a fluorescent compound, a bioluminescent compound, chemiluminescent compound, a metal chelator or an enzyme. Antibodies may also be conjugated to an anti-cancer pro-drug activating enzyme capable of converting the pro-drug to its active form. See, for example, U.S. Pat. No. 4,975,287.

Further, bi-specific antibodies specific for two or more SGP28 epitopes may be generated using methods generally known in the art. Further, antibody effector functions may be modified to enhance the therapeutic effect of SGP28 antibodies on cancer cells. For example, cysteine residues may be engineered into the Fc region, permitting the formation of interchain disulfide bonds and the generation of homodimers which may have enhanced capacities for internalization, ADCC and/or complement mediated cell killing (see, for example, Caron et al., 1992, J. Exp. Med. 176:1191–1195; Shopes, 1992, J. Immunol. 148: 2918–2922). Homodimeric antibodies may also be generated by cross-linking techniques known in the art (e.g., Wolff et al., Cancer Res. 53: 2560–2565).

SGP28 Transgenic Animals

Nucleic acids that encode SGP28 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding SGP28 can be used to clone genomic DNA encoding SGP28 in accordance with established techniques and the genomic sequences used to generate transgenic animals that contain cells that express DNA encoding SGP28.

Methods for generating transgenic animals, particularly animals such as mice or rats, have become conventional in the art and are described, for example, in U.S. Pat. Nos. 4,736,866 and 4,870,009. Typically, particular cells would be targeted for SGP28 transgene incorporation with tissue-specific enhancers. Transgenic animals that include a copy of a transgene encoding SGP28 introduced into the germ line of the animal at an embryonic stage can be used to examine the effect of increased expression of DNA encoding SGP28. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of SGP28 can be used to construct a SGP28 "knock out" animal that has a defective or altered gene encoding SGP28 as a result of homologous recombination between the endogenous gene encoding SGP28 and altered genomic DNA encoding SGP28 introduced into an embryonic cell of the animal. For example, cDNA encoding SGP28 can be used to clone genomic DNA encoding SGP28 in accordance with established techniques. A portion of the genomic DNA encoding SGP28 can be deleted or replaced with another gene, such as a gene encoding a selectable marker that can be used to monitor integration.

Typically, several kilobases of unaltered flanking DNA (both at the 5' and 3' ends) are included in the vector (see e.g., Thomas and Capecchi, 1987, Cell 51:503 for a description of homologous recombination vectors). The vector is introduced into an embryonic stem cell line (e.g., by electroporation) and cells in which the introduced DNA has homologously recombined with the endogenous DNA are selected (see e.g., Li et al., 1992, Cell 69:915). The selected cells are then injected into a blastocyst of an animal (e.g., a mouse or rat) to form aggregation chimeras (see e.g., Bradley, in Teratocarrinomas and Embryonic Stem Cells: A Practical Approach, E. J. Robertson, ed., IRL, Oxford, 1987, pp. 113–152).

A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the SGP28 polypeptide.

Assays for Circulating and Excreted SGP28

Based on applicants immunohistochemical evidence of high level lumenal expression of SGP28 in cancerous and precancerous prostate glands, it is expected that prostate tumors would secrete SGP28 into the vasculature and/or excrete SGP28 into urine or semen, where the protein may be detected and quantified using assays and techniques well known in the molecular diagnostic field. Detecting and quantifying the levels of circulating or excreted SGP28 is expected to have a number of uses in the diagnosis, staging, and prognosis of prostate cancer. A number of different technical approaches for the detection and quantification of proteins in serum, urine or semen are well known in the art.

Because SGP28 is a secreted protein expressed in cancers of the prostate and colon, and possibly other cancers, assays for detecting and quantifying SGP28 in blood or serum are expected to be useful for the detection, diagnosis, prognosis, and/or staging of a SGP28 expressing tumor in an individual. For example, SGP28 mRNA expression in normal tissues is found predominantly in prostate and ovary. However, high level protein expression is detected in prostate cancer as well as PIN. Accordingly, detection of serum SGP28 protein may provide an indication of the presence of a prostatic tumor. Diagnosis of cancer may be made on the basis of this information and/or other information. In respect of prostate cancer, for example, such other information may include serum PSA measurements, DRE and/or ultrasonography. Further, the level of SGP28 detected in the serum may provide information useful in staging or prognosis. For example, very high levels of SGP28 protein in serum may suggest a larger and/or more aggressive tumor.

In addition, peripheral blood may be conveniently assayed for the presence of SGP28 protein and/or SGP28 expressing cancer cells, including but not limited to prostate cancer, using RT-PCR to detect SGP28 expression. The presence of RT-PCR amplifiable SGP28 mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373–384; Ghossein et al., 1995, J. Clin. Oncol. 13: 1195–2000; Heston et al., 1995, Clin. Chem. 41: 1687–1688). RT-PCR assays are well known in the art.

In one embodiment, a capture ELISA is used to detect and quantify SGP28 in serum, urine or semen. A capture ELISA for SGP28 comprises, generally, at least two monoclonal antibodies of different isotypes that recognize distinct epitopes of the SGP28 protein, or one anti-SGP28 monoclonal antibody and a specific polyclonal serum derived from a different species (e.g., rabbit, goat, sheep, hamster, etc.). In this assay, one reagent serves as the capture (or coating) antibody and the other as the detection antibody.

As discussed in detail below, levels of SGP28 including SGP28 serum levels may be used to provide an indication of the presence, extent and aggressiveness of a SGP28 expressing tumor. As noted, above SGP28 shares a number of characteristics with PSA which is the most important, accurate, and clinically useful biochemical marker in the prostate. Any process that disrupts the normal architecture of the prostate allows diffusion of PSA into the stroma and microvasculature. Consequently, clinically important increases in serum prostate-specific antigen levels are seen with prostatic cancers. In particular, the greater number of malignant cells and the stromal disruption associated with cancer account for the increased serum prostate-specific antigen level. In this context, serum prostate-specific antigen levels correlate positively with clinical stage, tumor volume, histologic grade, and the presence of capsular perforation and seminal vesicle invasion. See e.g. Bostwick, D. G., 1994, Am. J. Clin. Pathol. 102(4 Suppl 1): S31–S37.

Using PSA as the best analogous molecule, it is likely that because SGP28 is also a secreted molecule that exhibits a restricted pattern of tissue expression (including the prostate), the increasing load of malignant cells and the stromal disruption that occurs with cancer will make the serum SGP28 antigen levels correlate positively with one or more clinically relevant factors such as clinical stage, tumor volume, histologic grade, and the presence of capsular perforation and seminal vesicle invasion. Serum SGP28 measurements over time would be expected to provide further information, wherein an increase in SGP28 would be expected to reflect progression and the rate of the increase would be expected to correlate with aggressiveness. Similarly, a decline in serum SGP28 would be expected to reflect a slower growing or regressing tumor. The identification of SGP28 in serum may be useful to detect tumor initiation and early stage disease. In patients who have undergone surgery or therapy, serum SGP28 levels would be useful for monitoring treatment response and potential recurrence.

Monitoring the Status of SGP28 and its Products

Assays that evaluate the status of the SGP28 gene and SGP28 gene products in an individual may provide information on the growth or oncogenic potential of a biological sample from this individual. For example, because SGP28 mRNA is so highly expressed in prostate cancers, and not in most normal tissue, assays that evaluate the relative levels of SGP28 mRNA transcripts or proteins in a biological sample may be used to diagnose a disease associated with SGP28 dysregulation, such as cancer, and may provide prognostic information useful in defining appropriate therapeutic options. Similarly, assays that evaluate the integrity SGP28 nucleotide and amino acid sequences in a biological sample, may also be used in this context.

The finding that SGP28 mRNA is so highly expressed in prostate cancers, and not in most normal tissue, provides evidence that this gene is associated with dysregulated cell growth and therefore identifies this gene and its products as targets that the skilled artisan can use to evaluate biological samples from individuals suspected of having a disease associated with SGP28 dysregulation. In another example, because the expression of SGP28 is normally restricted to prostate and ovary, one can also evaluate biological samples taken from other tissues to detect SGP28 expression as an indication of metastasis. In this context, the evaluation of the expression status of SGP28 gene and its products can be used to gain information on the disease potential of a tissue sample. The terms "expression status" in this context is used to broadly refer to the variety of factors involved in the expression, function and regulation of a gene and its products such as the level of mRNA expression, the integrity of the expressed gene products (such as the nucleic and amino acid sequences) and transcriptional and translational modifications to these molecules.

The expression status of SGP28 may provide information useful for predicting susceptibility to particular disease stages, progression, and/or tumor aggressiveness. The invention provides methods and assays for determining SGP28 expression status and diagnosing cancers that express SGP28, such as cancers of the prostate. SGP28 expression status in patient samples may be analyzed by a number of means well known in the art, including without limitation, immunohistochemical analysis, in situ hybridization, RT-PCR analysis on laser capture microdissected samples, western blot analysis of clinical samples and cell lines, and tissue array analysis. Typical protocols for evaluating the expression status of the SGP28 gene and gene products can be found, for example in *Current Protocols In Molecular Biology*, Units 2 [Northern Blotting], 4 [Southern Blotting], 15 [Immunoblotting] and 18 [PCR Analysis], Frederick M. Ausubul et al. eds., 1995.

In one aspect, the invention provides methods for monitoring SGP28 gene products by determining the status of SGP28 gene products expressed by cells in a test tissue sample from an individual suspected of having a disease associated with dysregulated cell growth (such as hyperplasia or cancer) and then comparing the status so determined to the status of SGP28 gene products in a corresponding normal sample, the presence of aberrant or altered status of SGP28 gene products in the test sample relative to the normal sample providing an indication of the presence of dysregulated cell growth within the cells of the individual.

The invention additionally provides methods of examining a biological sample for evidence of dysregulated cellular growth. In one embodiment, the method comprises comparing the status of SGP28 in the biological sample to the status of SGP28 in a corresponding normal sample, wherein alterations in the status of SGP28 in the biological sample are associated with dysregulated cellular growth. The status of SGP28 in the biological sample can be evaluated by, for example, examining levels of SGP28 mRNA expression or levels of SGP28 protein expression. In one embodiment, an alteration in the status of SGP28 is identified by the presence of SGP28 expressing cells in a biological sample from a tissue in which SGP28 expressing cells are normally absent.

In another aspect, the invention provides assays useful in determining the presence of cancer in an individual comprising detecting a significant increase in SGP28 mRNA or protein expression in a test cell or tissue sample relative to expression levels in the corresponding normal cell or tissue. The presence of SGP28 mRNA may, for example, be evaluated in tissue samples including but not limited to colon, lung, prostate, pancreas, bladder, breast, ovary, cervix, testis, head and neck, brain, stomach, bone, etc. The presence of significant SGP28 expression in any of these tissues may be useful to indicate the emergence, presence and/or severity of these cancers or a metastasis of cancer originating in another tissue, since the corresponding normal tissues do not express SGP28 mRNA or express it at lower levels.

In a related embodiment, SGP28 expression status may be determined at the protein level rather than at the nucleic acid level. For example, such a method or assay would comprise determining the level of SGP28 protein expressed by cells in a test tissue sample and comparing the level so determined to the level of SGP28 expressed in a corresponding normal sample. In one embodiment, the presence of SGP28 protein is evaluated, for example, using immunohistochemical methods. SGP28 antibodies or binding partners capable of detecting SGP28 protein expression may be used in a variety of assay formats well known in the art for this purpose.

In other related embodiments, one can evaluate the integrity SGP28 nucleotide and amino acid sequences in a biological sample in order to identify perturbations in the structure of these molecules such as insertions, deletions, substitutions and the like. Such embodiments are useful because perturbations in the nucleotide and amino acid sequences are observed in a large number of proteins associated with a growth dysregulated phenotype (see e.g. Marrogi et al., J. Cutan. Pathol. 26(8): 369–378 (1999)). In this context, a wide variety of assays for observing perturbations in nucleotide and amino acid sequences are well known in the art. For example, the size and structure of nucleic acid or amino acid sequences of SGP28 gene products may be observed by the northern, Southern, western, PCR and DNA sequencing protocols discussed herein. In addition, other methods for observing perturbations in nucleotide and amino acid sequences such as single strand conformation polymorphism analysis are well known in the art (see e.g. U.S. Pat. Nos. 5,382,510 and 5,952,170).

In another embodiment, one can examine the methylation status of the SGP28 gene in a biological sample. Aberrant demethylation and/or hypermethylation of CpG islands in gene 5' regulatory regions frequently occurs in immortalized and transformed cells and can result in altered expression of various genes. For example, promoter hypermethylation of the pi-class glutathione S-transferase (a protein expressed in normal prostate but not expressed in $>^90\%$ of prostate carcinomas) appears to permanently silence transcription of this gene and is the most frequently detected genomic alteration in prostate carcinomas (De Marzo et al., 1999, Am. J. Pathol. 155(6): 1985–1992). In addition, this alteration is present in at least 70% of cases of high-grade prostatic intraepithelial neoplasia (PEN) (Brooks et al., 1998, Cancer Epidemiol. Biomarkers Prev., 7:531–536).

In another example, expression of the LAGE-1 tumor specific gene (which is not expressed in normal prostate but is expressed in 25–50% of prostate cancers) is induced by deoxy-azacytidine in lymphoblastoid cells, suggesting that tumoral expression is due to demethylation (Lethe et al., 1998, Int J. Cancer 76(6): 903–908). In this context, a variety of assays for examining methylation status of a gene are well known in the art. For example, one can utilize in Southern hybridization approaches methylation-sensitive restriction enzymes which can not cleave sequences that contain methylated CpG sites in order to assess the overall methylation status of CpG islands.

In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in *Current Protocols In Molecular Biology*, Units 12, Frederick M. Ausubel et al. eds., 1995.

In another related embodiment, the invention provides assays useful in determining the presence of cancer in an individual, comprising detecting a significant change in the SGP28 alternative splice variants expressed in a test cell or tissue sample relative to expression levels in the corresponding normal cell or tissue. The monitoring of alternative splice variants of SGP28 is useful because changes in the alternative splicing of proteins is suggested as one of the steps in a series of events that lead to the progression of cancers (see e.g. Carstens et al., Oncogene 15(250: 3059–3065 (1997)).

Gene amplification provides an additional method of assessing the status of SGP28. Gene amplification may be measured in a sample directly, for example, by conventional Southern blotting, northern blotting to quantitate the transcription of mRNA [Thomas, *Proc. Natl. Acad. Sci. USA*, 77:5201–5205 (1980)], dot blotting (NA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

In addition to the tissues discussed above, peripheral blood may be conveniently assayed for the presence of cancer cells, including but not limited to prostate cancers, using RT-PCR to detect SGP28 expression. The presence of RT-PCR amplifiable SGP28 mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373–384; Ghossein et al., 1995, J. Clin. Oncol. 13: 1195–2000; Heston et al., 1995, Clin. Chem. 41: 1687–1688). RT-PCR assays are well known in the art.

A related aspect of the invention is directed to predicting susceptibility to developing cancer in an individual. In one embodiment, a method for predicting susceptibility to cancer comprises detecting SGP28 mRNA or SGP28 protein in a tissue sample, its presence indicating susceptibility to cancer, wherein the degree of SGP28 mRNA expression present is proportional to the degree of susceptibility. In a specific embodiment, the presence of SGP28 in prostate tissue is examined, with the presence of SGP28 in the sample providing an indication of prostate cancer susceptibility (or the emergence or existence of a prostate tumor). In a closely related embodiment, one can evaluate the integrity SGP28 nucleotide and amino acid sequences in a biological sample in order to identify perturbations in the structure of these molecules such as insertions, deletions, substitutions and the like, with the presence of one or more perturbations in SGP28 gene products in the sample providing an indication of cancer susceptibility (or the emergence or existence of a tumor).

Yet another related aspect of the invention is directed to methods for gauging tumor aggressiveness. In one embodiment, a method for gauging aggressiveness of a tumor comprises determining the level of SGP28 mRNA or SGP28 protein expressed by cells in a sample of the tumor, comparing the level so determined to the level of SGP28 mRNA or SGP28 protein expressed in a corresponding normal tissue taken from the same individual or a normal tissue reference sample, wherein the degree of SGP28 mRNA or SGP28 protein expression in the tumor sample relative to the normal sample indicates the degree of aggressiveness. In a specific embodiment, aggressiveness of prostate tumors is evaluated by determining the extent to which SGP28 is expressed in the tumor cells, with higher expression levels indicating more aggressive tumors. In a closely related embodiment, one can evaluate the integrity SGP28 nucleotide and amino acid sequences in a biological sample in order to identify perturbations in the structure of these molecules such as insertions, deletions, substitutions and the like, with the presence of one or more perturbations indicating more aggressive tumors.

Yet another related aspect of the invention is directed to methods for observing the progression of a malignancy in an individual over time. In one embodiment, methods for observing the progression of a malignancy in an individual over time comprise determining the level of SGP28 mRNA or SGP28 protein expressed by cells in a sample of the tumor, comparing the level so determined to the level of SGP28 mRNA or SGP28 protein expressed in an equivalent tissue sample taken from the same individual at a different time, wherein the degree of SGP28 mRNA or SGP28 protein expression in the tumor sample over time provides information on the progression of the cancer. In a specific embodiment, the progression of a cancer is evaluated by determining the extent to which SGP28 expression in the tumor cells alters over time, with higher expression levels indicating a progression of the cancer. In a closely related embodiment, one can evaluate the integrity SGP28 nucleotide and amino acid sequences in a biological sample in order to identify perturbations in the structure of these molecules such as insertions, deletions, substitutions and the like, with the presence of one or more perturbations indicating a progression of the cancer.

The above diagnostic approaches may be combined with any one of a wide variety of prognostic and diagnostic protocols known in the art. For example, another embodiment of the invention disclosed herein is directed to methods for observing a coincidence between the expression of SGP28 gene and SGP28 gene products (or perturbations in SGP28 gene and SGP28 gene products) and a factor that is associated with malignancy as a means of diagnosing and prognosticating the status of a tissue sample. In this context, a wide variety of factors associated with malignancy may be utilized such as the expression of genes otherwise associated with malignancy (including PSA, PSCA and PSM expression) as well as gross cytological observations (see e.g. Bocking et al., 1984, Anal. Quant. Cytol. 6(2):74–88; Epstein, 1995, Hum. Pathol. 1995 February; 26(2):223–9; Thorson et al., 1998, Mod. Pathol. 11(6):543–51; Baisden et al., 1999, Am. J. Surg. Pathol. 23(8):918–24). Methods for observing a coincidence between the expression of SGP28 gene and SGP28 gene products (or perturbations in SGP28 gene and SGP28 gene products) and an additional factor that is associated with malignancy are useful, for example, because the presence of a set or constellation of specific factors that coincide provides information crucial for diagnosing and prognosticating the status of a tissue sample.

In a typical embodiment, methods for observing a coincidence between the expression of SGP28 gene and SGP28 gene products (or perturbations in SGP28 gene and SGP28 gene products) and a factor that is associated with malignancy entails detecting the overexpression of SGP28 mRNA or protein in a tissue sample, detecting the overexpression of PSA mRNA or protein in a tissue sample, and observing a coincidence of SGP28 mRNA or protein and PSA mRNA or protein overexpression. In a specific embodiment, the expression of SGP28 and PSA mRNA in prostate tissue is examined. In a preferred embodiment, the coincidence of SGP28 and PSA mRNA overexpression in the sample provides an indication of prostate cancer, prostate cancer susceptibility or the emergence or existence of a prostate tumor.

Methods for detecting and quantifying the expression of SGP28 mRNA or protein are described herein and use standard nucleic acid and protein detection and quantification technologies well known in the art. Standard methods for the detection and quantification of SGP28 mRNA include in situ hybridization using labeled SGP28 riboprobes, northern blot and related techniques using SGP28 polynucleotide probes, RT-PCR analysis using primers specific for SGP28, and other amplification type detection methods, such as, for example, branched DNA, SISBA, TMA and the like. In a specific embodiment, semiquantitative RT-PCR may be used to detect and quantify SGP28 mRNA expression as described in the Examples that follow. Any number of primers capable of amplifying SGP28 may be used for this purpose, including but not limited to the various primer sets specifically described herein. Standard methods for the detection and quantification of protein may be used for this purpose. In a specific embodiment, polyclonal or monoclonal antibodies specifically reactive with the wild-type SGP28 protein may be used in an immunohistochemical assay of biopsied tissue. Antibodies directed against SGP28 protein can also be used to detect SGP28 in a patient specimen (e.g., blood, urine, semen or other sample) using conventional techniques such as fluorescence-activated cell sorting (FACS) and/or ELISA.

Identifying Molecules that Interact with SGP28

The SGP28 protein sequences disclosed herein allow the skilled artisan to identify proteins, small molecules and other agents that interact with SGP28 and pathways activated by SGP28 via any one of a variety of art accepted protocols. For example one can utilize one of the variety of so-called interaction trap systems (also referred to as the "two-hybrid assay"). In such systems, molecules that interact reconstitute a transcription factor and direct expression of a reporter gene, the expression of which is then assayed. Typical systems identify protein—protein interactions in vivo through reconstitution of a eukaryotic transcriptional activator and are disclosed for example in U.S. Pat. Nos. 5,955,280, 5,925,523, 5,846,722 and 6,004,746.

Alternatively one can identify molecules that interact with SGP28 protein sequences by screening peptide libraries. In such methods, peptides that bind to selected receptor molecules such as SGP28 are identified by screening libraries that encode a random or controlled collection of amino acids. Peptides encoded by the libraries are expressed as fusion proteins of bacteriophage coat proteins, and bacteriophage particles are then screened against the receptors of interest. Peptides having a wide variety of uses, such as therapeutic or diagnostic reagents, may thus be identified without any prior information on the structure of the expected ligand or receptor molecule. Typical peptide libraries and screening methods that can be used to identify molecules that interact with SGP28 protein sequences are disclosed for example in U.S. Pat. Nos. 5,723,286 and 5,733,731.

Alternatively, cell lines expressing SGP28 can be used to identify protein—protein interactions mediated by SGP28. This possibility can be examined using immunoprecipitation techniques as shown by others (Hamilton B J, et al. Biochem. Biophys. Res. Commun. 1999, 261:646–51). Typically SGP28 protein can be immunoprecipitated from SGP28 expressing prostate cancer cell lines using anti-SGP28 antibodies. Alternatively, antibodies against His-tag can be used in a cell line engineered to express SGP28 (vectors mentioned above). The immunoprecipitated complex can be examined for protein association by procedures such as western blotting, $^{35}$S-methionine labeling of proteins, protein microsequencing, silver staining and two dimensional gel electrophoresis.

Small molecules that interact with SGP28 can be identified through related embodiments of such screening assays. For example, small molecules can be identified that interfere with SGP28 function, including molecules that interfere with SGP28's ability to bind to cells and/or to modulate tumor formation, progression, migration and/or apoptosis. Typical methods are discussed for example in U.S. Pat. No. 5,928,868 and include methods for forming hybrid ligands in which at least one ligand is a small molecule. In an illustrative embodiment, the hybrid ligand is introduced into cells that in turn contain a first and a second expression vector. Each expression vector includes DNA for expressing a hybrid protein that encodes a target protein linked to a coding sequence for a transcriptional module. The cells further contains a reporter gene, the expression of which is conditioned on the proximity of the first and second hybrid proteins to each other, an event that occurs only if the hybrid ligand binds to target sites on both hybrid proteins. Those cells that express the reporter gene are selected and the unknown small molecule or the unknown hybrid protein is identified.

A typical embodiment of this invention consists of a method of screening for a molecule that interacts with a SGP28 amino acid sequence shown in Table 2 (SEQ ID NO: 3), comprising the steps of contacting a population of molecules with the SGP28 amino acid sequence, allowing the population of molecules and the SGP28 amino acid sequence to interact under conditions that facilitate an interaction, determining the presence of a molecule that interacts with the SGP28 amino acid sequence and then separating molecules that do not interact with the SGP28 amino acid sequence from molecules that do interact with the SGP28 amino acid sequence. In a specific embodiment, the method further includes purifying a molecule that interacts with the SGP28 amino acid sequence. In a preferred embodiment, the SGP28 amino acid sequence is contacted with a library of peptides. Additional assays for identifying molecules that modulate SGP28 function are described in the Examples that follow.

Therapeutic Methods and Compositions

The identification of SGP28 as a prostate cancer protein opens a number of therapeutic approaches to the treatment of prostate cancers. As discussed above, SGP28 is a secreted protein, and its interaction with other cells and molecules likely plays a role in the regulation of the prostate environment and the initiation, development and/or progression of cancer. SGP28 can be targeted for therapy via approaches aimed at inhibiting activity of the SGP28 protein, inhibiting the binding or association of SGP28 protein with other cells and molecules, inhibiting transcription or translation of SGP28, and/or via the use of cancer vaccines based on SGP28. The therapeutic strategy can thus be designed to inhibit a function of the molecule or to target the SGP28 molecule itself.

The expression profile of SGP28 is reminiscent of the MAGEs, PSA and PMSA, which are tissue-specific genes that are up-regulated in melanomas and other cancers (Van den Eynde and Boon, Int J Clin Lab Res. 27:81–86, 1997). Due to their tissue-specific expression and high expression levels in cancer, these molecules are currently being investigated as targets for cancer vaccines (Durrant, Anticancer Drugs 8:727–733, 1997; Reynolds et al., Int J Cancer 72:972–976, 1997). The expression pattern of SGP28 provides evidence that it is likewise an ideal target for a cancer vaccine approach to prostate cancer, as its expression is not detected in most normal tissues.

Accordingly, therapeutic approaches targeting particular motifs of SGP28, or aimed at inhibiting the activity of the SGP28 protein, are expected to be useful for patients suffering from prostate cancer and other cancers expressing SGP28. The therapeutic approaches aimed at inhibiting the activity of the SGP28 protein generally fall into two classes. One class comprises various methods for inhibiting the binding or association of the SGP28 protein with its binding partner or with other proteins. Another class comprises a variety of methods for inhibiting the transcription of the SGP28 gene or translation of SGP28 mRNA.

SGP28 as a Target for Antibody-Based Therapy

The SGP28 molecule is an attractive target for antibody-based therapeutic strategies. Because SGP28 is expressed in cancer cells and not in most normal tissues, systemic administration of SGP28-immunoreactive compositions would be expected to exhibit excellent sensitivity without toxic, nonspecific and/or non-target effects caused by binding of the immunotherapeutic molecule to non-target organs and tissues. Antibodies specifically reactive with SGP28 can be useful to treat SGP28-expressing cancers systemically, either as conjugates with a toxin or therapeutic agent, or as naked antibodies capable of inhibiting interaction of SGP28 with its binding partner.

SGP28 antibodies can be introduced into a patient such that the antibody binds to SGP28 and eliminates SGP28 function in the primary tumor, in circulating micrometastases, and/or in established metastases. The degree of tumor vascularization may provide guidance on which delivery approach is recommended. Similarly, the grade and/or stage of disease would be expected to provide useful information in this regard. For example, a higher grade, more advanced tumor may be more likely to seed metastases, suggesting systemic administration in order to treat or prevent the emergence of metastases.

Cancer immunotherapy using anti-SGP28 antibodies may follow the teachings generated from various approaches that have been successfully employed in the treatment of other types of cancer, including but not limited to colon cancer (Arlen et al., 1998, Crit. Rev. Immunol. 18:133–138), multiple myeloma (Ozaki et al., 1997, Blood 90:3179–3186; Tsunenari et al., 1997, Blood 90:2437–2444), gastric cancer (Kasprzyk et al., 1992, Cancer Res. 52:2771–2776), B-cell lymphoma (Funakoshi et al., 1996, J. Immunother. Emphasis Tumor Immunol. 19:93–101), leukemia (Zhong et al., 1996, Leuk. Res. 20:581–589), colorectal cancer (Moun et al., 1994, Cancer Res. 54:6160–6166); Velders et al., 1995, Cancer Res. 55:4398–4403), and breast cancer (Shepard et al., 1991, J. Clin. Immunol. 11:117–127). Some therapeutic approaches involve conjugation of naked antibody to a toxin, such as the conjugation of $^{131}$I to anti-CD20 antibodies (e.g., Bexxar™, Coulter Pharmaceutical™), while others involve co-administration of antibodies and other therapeutic agents, such as Herceptin™ (trastuzumab) with paclitaxel (Genentech,™ Inc.). For treatment of prostate cancer, for example, SGP28 antibodies can be administered in conjunction with radiation, chemotherapy or hormone ablation.

Although SGP28 antibody therapy may be useful for all stages of cancer, antibody therapy may be particularly appropriate in advanced or metastatic cancers. Treatment with the antibody therapy of the invention may be indicated for patients who have received previously one or more chemotherapy, while combining the antibody therapy of the invention with a chemotherapeutic or radiation regimen may be preferred for patients who have not received chemotherapeutic treatment. Additionally, antibody therapy may enable the use of reduced dosages of concomitant chemotherapy, particularly for patients who do not tolerate the toxicity of the chemotherapeutic agent very well.

It may be desirable for some cancer patients to be evaluated for the presence and level of SGP28 expression, preferably using immunohistochemical assessments of tumor tissue, quantitative SGP28 imaging, or other techniques capable of reliably indicating the presence and degree of SGP28 expression. Immunohistochemical analysis of tumor biopsies or surgical specimens may be preferred for this purpose. Methods for immunohistochemical analysis of tumor tissues are well known in the art.

Anti-SGP28 monoclonal antibodies useful in treating prostate and other cancers include those that are capable of initiating a potent immune response against the tumor and those that are capable of direct cytotoxicity. In this regard, anti-SGP28 monoclonal antibodies (mAbs) may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-SGP28 mAbs that exert a direct biological effect on tumor growth are useful in the practice of the invention. Potential mechanisms by which such directly cytotoxic mAbs may act include inhibition of cell growth, modulation of cellular differentiation, modulation of tumor angiogenesis factor profiles, and the induction of apoptosis. The mechanism by which a particular anti-SGP28 mAb exerts an anti-tumor effect may be evaluated using any number of in vitro assays designed to determine ADCC, ADMMC, complement-mediated cell lysis, and so forth, as is generally known in the art The use of murine or other non-human monoclonal antibodies, or human/mouse chimeric mAbs may induce moderate to strong immune responses in some patients. In some cases, this will result in clearance of the antibody from circulation and reduced efficacy. In the most severe cases, such an immune response may lead to the extensive formation of immune complexes that, potentially, can cause renal failure. Accordingly, preferred monoclonal antibodies used in the practice of the therapeutic methods of the invention are those that are either fully human or humanized and that bind specifically to the target SGP28 antigen with high affinity but exhibit low or no antigenicity in the patient.

Therapeutic methods of the invention contemplate the administration of single anti-SGP28 mAbs as well as combinations, or cocktails, of different mAbs. Such mAb cocktails may have certain advantages inasmuch as they contain mAbs that target different epitopes, exploit different effector mechanisms or combine directly cytotoxic mAbs with mAbs that rely on immune effector functionality. Such mAbs in combination may exhibit synergistic therapeutic effects. In addition, the administration of anti-SGP28 mAbs may be combined with other therapeutic agents, including but not limited to various chemotherapeutic agents, androgen-blockers, and immune modulators (e.g., IL-2, GM-CSF). The anti-SGP28 mAbs may be administered in their "naked" or unconjugated form, or may have therapeutic agents conjugated to them.

The anti-SGP28 antibody formulations may be administered via any route capable of delivering the antibodies to the tumor site. Potentially effective routes of administration include, but are not limited to, intravenous, intraperitoneal, intramuscular, intratumor, intradermal, and the like. Treatment will generally involve the repeated administration of the anti-SGP28 antibody preparation via an acceptable route of administration such as intravenous injection (IV), typically at a dose in the range of about 0.1 to about 10 mg/kg body weight. Doses in the range of 10–500 mg mAb per week may be effective and well tolerated.

Based on clinical experience with the Herceptin mAb in the treatment of metastatic breast cancer, an initial loading dose of approximately 4 mg/kg patient body weight IV followed by weekly doses of about 2 mg/kg IV of the anti-SGP28 mAb preparation may represent an acceptable dosing regimen. Preferably, the initial loading dose is administered as a 90 minute or longer infusion. The periodic maintenance dose may be administered as a 30 minute or longer infusion, provided the initial dose was well tolerated. However, as one of skill in the art will understand, various factors will influence the ideal dose regimen in a particular case. Such factors may include, for example, the binding affinity and half life of the Ab or mAbs used, the degree of SGP28 expression in the patient, the extent of circulating shed SGP28 antigen, the desired steady-state antibody concentration level, frequency of treatment, and the influence of chemotherapeutic agents used in combination with the treatment method of the invention.

Optimally, patients should be evaluated for the level of circulating shed SGP28 antigen in serum in order to assist in the determination of the most effective dosing regimen and related factors. Such evaluations may also be used for monitoring purposes throughout therapy, and may be useful to gauge therapeutic success in combination with evaluating other parameters (such as serum PSA levels in prostate cancer therapy).

Inhibition of SGP28 Protein Function

The invention includes various methods and compositions for inhibiting the binding of SGP28 to its binding partner or ligand, or its association with other protein(s) as well as methods for inhibiting SGP28 function.

Inhibition of SGP28 with Recombinant Proteins

In one approach, recombinant molecules that are capable of binding to SGP28 thereby preventing SGP28 from accessing/binding to its binding partner(s) or associating with other protein(s) are used to inhibit SGP28 function. Such recombinant molecules may, for example, contain the reactive part(s) of a SGP28 specific antibody molecule. In a particular embodiment, the SGP28 binding domain of a SGP28 binding partner may be engineered into a dimeric fusion protein comprising two SGP28 ligand binding domains linked to the Fc portion of a human IgG, such as human IgG1. Such IgG portion may contain, for example, the $C_H2$ and $C_H3$ domains and the hinge region, but not the $C_H1$ domain. Such dimeric fusion proteins may be administered in soluble form to patients suffering from a cancer associated with the expression of SGP28, including but not limited to prostate cancer, where the dimeric fusion protein specifically binds to SGP28 thereby blocking SGP28 interaction with a binding partner. Such dimeric fusion proteins may be further combined into multimeric proteins using known antibody linking technologies.

Inhibition of SGP28 with Intracellular Antibodies

In another approach, recombinant vectors encoding single chain antibodies that specifically bind to SGP28 may be introduced into SGP28 expressing cells via gene transfer technologies, wherein the encoded single chain anti-SGP28 antibody is expressed intracellularly, binds to SGP28 protein, and thereby inhibits its function. Methods for engineering such intracellular single chain antibodies are well known. Such intracellular antibodies, also known as "intrabodies", may be specifically targeted to a particular compartment within the cell, providing control over where the inhibitory activity of the treatment will be focused. This technology has been successfully applied in the art (for review, see Richardson and Marasco, 1995, TIBTECH vol. 13). Intrabodies have been shown to virtually eliminate the expression of otherwise abundant cell surface receptors. See, for example, Richardson et al., 1995, Proc. Natl. Acad. Sci. USA 92: 3137–3141; Beerli et al., 1994, J. Biol. Chem. 289: 23931–23936; Deshane et al., 1994, Gene Ther. 1: 332–337.

Single chain antibodies comprise the variable domains of the heavy and light chain joined by a flexible linker polypeptide, and are expressed as a single polypeptide. Optionally, single chain antibodies may be expressed as a single chain variable region fragment joined to the light chain constant region. Well known intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif. Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In one embodiment, SGP28 intrabodies are designed to bind specifically to a particular SGP28 domain. For example, cytosolic intrabodies that specifically bind to the SGP28 protein may be used to prevent SGP28 related molecules from gaining access to the nucleus, thereby preventing it from exerting any biological activity within the nucleus.

In order to direct the expression of such intrabodies specifically to particular tumor cells, the transcription of the intrabody may be placed under the regulatory control of an appropriate tumor-specific promoter and/or enhancer. In order to target intrabody expression specifically to prostate, for example, the PSA promoter and/or promoter/enhancer may be utilized (See, for example, U.S. Pat. No. 5,919,652).

Inhibition of SGP28 Transcription or Translation

Within another class of therapeutic approaches, the invention provides various methods and compositions for inhibiting the transcription of the SGP28 gene. Similarly, the invention also provides methods and compositions for inhibiting the translation of SGP28 mRNA into protein.

In one approach, a method of inhibiting the transcription of the SGP28 gene comprises contacting the SGP28 gene with a SGP28 antisense polynucleotide. In another approach, a method of inhibiting SGP28 mRNA translation comprises contacting the SGP28 mRNA with an antisense polynucleotide. In another approach, a SGP28 specific ribozyme may be used to cleave the SGP28 message, thereby inhibiting translation. Such antisense and ribozyme based methods may also be directed to the regulatory regions of the SGP28 gene, such as the SGP28 promoter and/or enhancer elements. Similarly, proteins capable of inhibiting a SGP28 gene transcription factor may be used to inhibit SGP28 mRNA transcription. The various polynucleotides and compositions useful in the aforementioned methods have been described above. The use of antisense and ribozyme molecules to inhibit transcription and translation is well known in the art.

Other factors that inhibit the transcription of SGP28 through interfering with SGP28 transcriptional activation may also be useful for the treatment of cancers expressing SGP28. Similarly, factors that are capable of interfering with SGP28 processing may be useful for the treatment of cancers expressing SGP28. Cancer treatment methods utilizing such factors are also within the scope of the invention.

General Considerations for Therapeutic Strategies

Gene transfer and gene therapy technologies may be used for delivering therapeutic polynucleotide molecules to tumor cells synthesizing SGP28 (i.e., antisense, ribozyme, polynucleotides encoding intrabodies and other SGP28 inhibitory molecules). A number of gene therapy approaches are known in the art. Recombinant vectors encoding SGP28 antisense polynucleotides, ribozymes, factors capable of interfering with SGP28 transcription, and so forth, may be delivered to target tumor cells using such gene therapy approaches.

The above therapeutic approaches may be combined with any one of a wide variety of chemotherapy or radiation therapy regimens. These therapeutic approaches may also enable the use of reduced dosages of chemotherapy and/or less frequent administration, particularly in patients that do not tolerate the toxicity of the chemotherapeutic agent well.

The anti-tumor activity of a particular composition (e.g., antisense, ribozyme, intrabody), or a combination of such compositions, may be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of SGP28 to a binding partner, etc.

In vivo, the effect of a SGP28 therapeutic composition may be evaluated in a suitable animal model. For example, xenogeneic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402–408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays that measure inhibition of tumor formation, tumor regression or metastasis, and the like. See, also, the Examples below.

In vivo assays that qualify the promotion of apoptosis may also be useful in evaluating potential therapeutic compositions. In one embodiment, xenografts from bearing mice treated with the therapeutic composition may be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods may be formulated into pharmaceutical compositions, including vaccine compositions, comprising a carrier suitable for the desired delivery method. Suitable carriers include any material that when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences $16^{th}$ Edition, A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

Cancer Vaccines

The invention further provides cancer vaccines comprising a SGP28 protein or fragment thereof, as well as DNA based vaccines. In view of the prostate- and tumor-restricted expression of SGP28, SGP28 cancer vaccines are expected to be effective at specifically preventing and/or treating SGP28 expressing cancers without creating non-specific effects on non-target tissues. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63: 231–237; Fong et al., 1997, J. Immunol. 159: 3113–3117). Such methods can be readily practiced by employing a SGP28 protein, or fragment thereof, or a SGP28 encoding nucleic acid molecule and recombinant vectors capable of expressing and appropriately presenting the SGP28 immunogen.

For example, viral gene delivery systems may be used to deliver a SGP28-encoding nucleic acid molecule. Various viral gene delivery systems that can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658–663). Non-viral delivery systems may also be employed by using naked DNA encoding a SGP28 protein or fragment thereof introduced into the patient (e.g., intramuscularly) to induce an anti-tumor response. In one embodiment, the full-length a human SGP28 cDNA may be employed.

In one embodiment, a SGP28 cancer vaccine is based on the identification of immunogenic peptides within the SGP28 amino acid sequence shown in Table 2 (SEQ ID NO: 3). As discussed further in the examples below, SGP28 has been shown to induce T and B cell responses. A recombinant HIS-tagged protein including the ORF of SGP28 (Table 2; SEQ ID NO: 3) has been used to generate an immune response in mice for the production of monoclonal antibodies. Amino acids 93–107 of SGP28 (CNYRHSNPKDRMTSL; SEQ ID NO: 27), have been used to generate an immune response in rabbits for the production of polyclonal antibodies. Thus, specific portions of SGP28, and polynucleotides encoding these portions, may be selected for the production of a cancer vaccine.

In another embodiment, SGP28 nucleic acid molecules encoding specific cytotoxic T lymphocyte (CTL) epitopes may be employed. CTL epitopes can be determined using specific algorithms (e.g., Epimer, Brown University) to identify peptides within a SGP28 protein that are capable of optimally binding to specified HLA alleles. One suitable algorithm is the HLA Peptide Motif Search algorithm available at the Bioinformatics and Molecular Analysis Section BIMAS) web site. This algorithm is based on binding of specific peptide sequences in the groove of HLA Class I molecules and specifically HLA-A2 (Falk et al., 1991, Nature 351:290–6; Hunt et al., 1992, Science 255:1261–3; Parker et al., 1992, J. Immunol. 149:3580–7; Parker et al., 1994, J. Immunol. 152:163–75). The HLA Peptide Motif Search algorithm allows location and ranking of 8-mer, 9-mer, and 10-mer peptides from a complete protein sequence for predicted binding to HLA-A2 as well as other Class I molecules. Most HLA-A2 binding peptides are 9-mers, favorably containing a leucine at position 2 and a valine or leucine at position 9 (Parker et al., 1992, J. Immunol. 149:3580–7). Actual binding of peptides to HLA-A2 can be evaluated by stabilization of HLA-A2 expression on the antigen processing defective cell line T2 (Xue et al., 1997, Prostate 30:73–8; Peshwa et al., 1998, Prostate 36:129–38). Immunogenicity of specific peptides can be evaluated in vitro by stimulation of CD8+ CTL in the presence of dendritic cells (Xue et al.; Peshwa et al., supra).

Specific SGP28 peptides predicted to bind HLA-A2 and preferred for use in cancer 1 vaccines include peptides corresponding to amino acids 2–10 (TLFPVLLFL; SEQ ID NO: 17), amino acids 6–14 (VLLFLVAGL; SEQ ID NO: 18), amino acids 30–38 (ALLTTQTQV; SEQ ID NO: 19), amino acids 142–150 (VVWYSSYLV; SEQ ID NO: 20), amino acids 222–230 (TLTCKHQLV; SEQ ID NO: 21), amino acids 175–183 (GNWANRLYV; SEQ ID NO: 22), amino acids 7–15 (LLFLVAGLL; SEQ ID NO: 23), amino acids 141–149 (QVVWYSSYL; SEQ ID NO: 24), amino acids 134–142 (AVVGHYTQV; SEQ ID NO: 25), and amino acids 211–219 (DLYSNCKSL; SEQ ID NO: 26) of the SGP28 protein sequence shown in Table 2.

Various ex vivo strategies may also be employed. One approach involves the use of dendritic cells to present SGP28 antigen to a patient's immune system. Dendritic cells express MHC class I and II, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65–69; Murphy et al., 1996, Prostate 29: 371–380). Dendritic cells can be used to present SGP28 peptides to T cells in the context of MHC class I and II molecules. In one embodiment, autologous dendritic cells are pulsed with SGP28 peptides capable of binding to MHC molecules. In another embodiment, dendritic cells axe pulsed with the complete SGP28 protein. Yet another embodiment involves engineering the overexpression of the SGP28 gene in dendritic cells using various implementing vectors known in the art, such as adenovirus (Arthur et al., 1997, Cancer Gene Ther. 4: 17–25), retrovirus (Henderson et al., 1996, Cancer Res. 56: 3763–3770), lentivirus, adeno-associated virus, DNA transfection (Ribas et al., 1997, Cancer Res. 57: 2865–2869), and tumor-derived RNA transfection (Ashley et al., 1997, J. Exp. Med. 186: 1177–1182). Cells expressing SGP28 may also be engineered to express immune modulators, such as GM-CSF, and used as immunizing agents.

Anti-idiotypic anti-SGP28 antibodies can also be used in anti-cancer therapy as a vaccine for inducing an immune response to cells expressing a SGP28 protein. Specifically, the generation of anti-idiotypic antibodies is well known in the art and can readily be adapted to generate anti-idiotypic anti-SGP28 antibodies that mimic an epitope on a SGP28 protein (see, for example, Wagner et al., 1997, Hybridoma 16: 33–40; Foon et al., 1995, J Clin Invest 96: 334–342; Herlyn et al., 1996, Cancer Immunol Immunother 43: 65–76). Such an anti-idiotypic antibody can be used in cancer vaccine strategies.

Genetic immunization methods may be employed to generate prophylactic or therapeutic humoral and cellular immune responses directed against cancer cells expressing SGP28. Constructs comprising DNA encoding a SGP28 protein/immunogen and appropriate regulatory sequences may be injected directly into muscle or skin of an individual, such that the cells of the muscle or skin take up the construct and express the encoded SGP28 protein/immunogen. Expression of the SGP28 protein immunogen results in the generation of prophylactic or therapeutic humoral and cellular immunity against prostate and other SGP28-expressing cancers. Various prophylactic and therapeutic genetic immunization techniques known in the art may be used.

Diagnostic Compositions and Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a SGP28 protein or a SGP28 gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the on the container to indicate that the composition is used for a specific therapy or non-therapeutic application, and may also indicate directions for either in vivo or in vitro use, such as those described above.

Accordingly, the invention also provides diagnostic compositions comprising SGP28->related molecules. Such molecules include the various SGP28 polynucleotides, primers, probes, proteins, fragments, antibodies described herein. The molecules included in the diagnostic composition may optionally be labeled with a detectable marker. SGP28 diagnostic compositions may further comprise appropriate buffers, diluents, and other ingredients as desired.

EXAMPLES

Various aspects of the invention are further described and illustrated by way of the several examples that follow, none of which are intended to limit the scope of the invention.

Example 1

SSH-Generated Isolation of cDNA Fragment of the SGP28 Gene

Materials and Methods

LAPC Xenografts:

LAPC xenografts were obtained from Dr. Charles Sawyers (UCLA) and generated as described (Klein et al, 1997, Nature Med. 3: 402–408; Craft et al., 1999, Cancer Res. 59: 5030–5036). Androgen dependent and independent LAPC-4 xenografts (LAPC-4 AD and AI, respectively) and LAPC-9 xenografts (LAPC-9 AD and AI, respectively) were grown in intact male SCID mice or in castrated males, respectively, and were passaged as small tissue chunks in recipient males. LAPC-4 AI xenografts were derived from LAPC-4 AD tumors and LAPC-9 AI xenografts were derived from LAPC-9 AD tumors. To generate the AI xenografts, male mice bearing LAPC AD tumors were castrated and maintained for 2–3 months. After the LAPC tumors re-grew, the tumors were harvested and passaged in castrated males or in female SCID mice.

LAPC-4 AD xenografts were grown intratibially as follows. LAPC-4 AD xenograft tumor tissue grown subcutaneously was minced into 1–2 mm$^3$ sections while the tissue was bathed in 1X Iscoves medium, minced tissue was then centrifuged at 1.3K rpm for 4 minutes, the supernatant was resuspended in 10 ml ice cold 1X Iscoves medium and centrifuged at 1.3K rpm for 4 minutes. The pellet was then resuspended in 1X Iscoves with 1% pronase E and incubated for 20 minutes at room temperature with mild rocking agitation followed by incubation on ice for 2–4 minutes.

Filtrate was centrifuged at 1.3K rmp for 4 minutes, and the pronase was removed from the aspirated pellet by resuspending in 10 ml Iscoves and re-centrifuging. Clumps of cells were then plated in PrEGM medium and grown overnight. The cells were then harvested, filtered, washed 2X RPMI, and counted. Approximately 50,000 cells were mixed with and equal volume of ice-cold Matrigel on ice, and surgically injected into the proximal tibial metaphyses of SCID mice via a 27 gauge needle. After 10–12 weeks, LAPC-4 tumors growing in bone marrow were recovered.

Cell Lines:

Human cell lines (e.g., HeLa) were obtained from the ATCC and were maintained in DMEM with 5% fetal calf serum.

RNA Isolation:

Tumor tissue and cell lines were homogenized in TRI-ZOL® reagent (Life Technologies, Gibco BRL™; TRI-ZOL® reagent is a monophasic solution of phenol and guanidine isothiocyanate suitable for isolating total RNA, DNA, and proteins) using 10 ml/g tissue or $10 \text{ ml}/10^8$ cells to isolate total RNA. Poly A RNA was purified from total RNA using QIAGEN™'S OLIGOTEX™ mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.
DPNCDN (cDNA Synthesis Primer):
5'TTTTGATCAAGCTT$_{30}$3' (SEQ ID NO: 28)
Adaptor 1:
5'CTAATACGACTCACTATAGGGCTC-GAGCGGCCGCCCGGGCAG3' 3'GGCCCGTCCTAG5' (SEQ ID NO: 29,30)
Adaptor 2:
5'GTAATACGACTCACTATAGGGCAGCGTG-GTCGCGGCCGAG3' 3'CGGCTCCTAG5' (SEQ ID NO: 31,32)
PCR primer 1:
5'CTAATACGACTCACTATAGGGC3' (SEQ ID NO: 33)
Nested Primer (NP)1:
5'TCGAGCGGCCGCCCGGGCAGGA3' (SEQ ID NO: 34)
Nested Primer (NP)2:
5'AGCGTGGTCGCGGCCGAGGA3' (SEQ ID NO: 35)

Suppression Subtractive Hybridization:

Suppression Subtractive Hybridization (SSH) was used to identify cDNAs corresponding to genes which may be differentially expressed in prostate cancer. The SSH reaction utilized cDNA from LAPC-4 AD xenografts growing in two different environments, namely the subcutaneous ("LAPC-4 AD SQ") and intratibial ("LAPC-4 AD IT") growth environments, wherein the LAPC-4 AD IT xenograft was used as the source of the "tester" cDNA, while the LAPC-4 AD SQ xenograft was used as the source of the "driver" cDNA.

Double stranded cDNAs corresponding to tester and driver cDNAs were synthesized from 2 μg of poly(A)+ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs. at 37° C. Digested cDNA was extracted with phenol/chloroform (1:1) and ethanol precipitated.

Driver cDNA was generated by combining in a 1:1 ratio Dpn II digested cDNA from the relevant xenograft source (see above) with a mix of digested cDNAs derived from human benign prostatic hyperplasia (BPH), the human cell lines HeLa, 293, A431, Colo205, and mouse liver.

Tester cDNA was generated by diluting 1 μl of Dpn II digested cDNA from the relevant xenograft source (see above) (400 ng) in 5 μl of water. The diluted cDNA (2 μl, 160 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification. Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10–12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

Results

The SSH experiment described in the Materials and Methods, supra, led to the isolation of numerous candidate gene fragment clones (SSH clones). All candidate clones were sequenced and subjected to homology analysis against all sequences in the major public gene and EST databases in order to provide information on the identity of the corresponding gene and to help guide the decision to analyze a particular gene for differential expression. In general, gene fragments which had no homology to any known sequence in any of the searched databases, and thus considered to represent novel genes, as well as gene fragments showing homology to previously sequenced expressed sequence tags (ESTs), were subjected to differential expression analysis by RT-PCR and/or Northern analysis.

One of the SSH clones was identical to the corresponding sequence of a secreted In molecule known as specific granule protein 28 (SGP28) (Kjeldsen et al., 1996, FEBS Lett. 380, 246–250) or cysteine-rich secretory protein (CRISP-3) (Kratzschmar et al., 1996, Eur J Biochem 236 (3):827–36). The sequence of this clone (36P1G3) is as follows:
GATCTCTATAGTAACTGTAAAAGT-
TGAAGCTCACATTAACCTGTAAACATCAG
TTGGTCAGGGACAGTTGCAAGGCCTCCT-
GCAATTGTTCAAACAGCATTTATTA
AATACGCATTACACACCGAGTAGGGC-
TATGTAGAGAGGAGTCAGATTATCTAC
TTAGATTTGGCATCTACTTAGATITAA-
CATATACTAGCTGAGAAATFGTAGGCA
TGTTTGATACACATTTGATTTCAAATGT-
FTTCTTCTGGATC (SEQ ID NO: 1).

Example 2

Isolation of Full Length SGP28 Encoding cDNA

A full length cDNA (clone 1; Table 1) of 774 bp was isolated from a prostate library, revealing an ORF of 258 amino acids (Table 2). The sequence identified herein differs from the published SGP28 sequence (Kjeldsen et al., 1996, FEBS Lett. 380(3):246–50) in two nucleic acids, one in the coding sequence and one in the 5' UTR. These differences do not alter the protein sequence.

Table 1: Full Length 36P1G3/SGP28 cDNA (SEQ ID NO: 2)
TGATGAAACAAATACTTCATCCT-
GCTCTGGAAACCACTGCAATGACATTATTCC
CAGTGCTGTFGITCCTGGTTGCTGGGCT-
GCTTCCATCTTTTCCAGCAAATGAA
GATAAGGATCCCGCTFTTACTGCTTTGT-
TAACCACCCAAACACAAGTGCAAAG
GGAGATTGTGAATAAGCACAATGAACT-
GAGGAGAGCAGTATCTCCCCCTGCCA
GAAACATGCTGAAGATGGAATGGAA-
CAAAGAGGCTGCAGCAAATGCCCAAAA
GTGGGCAAACCAGTGCAATTACAGACA-
CAGTAACCCAAAGGATCGAATGACA
AGTCTAAAATGTGGTGAGAATCTCTA-
CATGTCAAGTGCCCCCAGCTCATGGTC
ACAAGCAATCCAAAGCTGGTMTGATGAG-
TACAATGATTTTGACTTTGGTGTAG
GGCCAAAGACTCCCAACGCAGTGGTTG-
GACAMIATACACAGGTTGTTTTGGTAC
TCTTCATACCTCGTTGGATGTGGAAAT-
GCCTACTGTCCCAATCAAAAAGTTCTA
AAATACTACTATGTTTGCCAATATTGTC-
CTGCTGGTAATTGGGCTAATAGACTA TATGTC-
CCTTATGAACAAGGAGCACCTTGTGC-
CAGTTGCCCAGATAACTGTGA
CGATGGACTATGCACCAATGGTTGCAAG-
TACGAAGATCTCTATAGTAACTGTA
AAAGTTTGAAGCTCACATTAACCTG-
TATACATCAGTTGGTCAGGGACAGTTGC
AAGGCATCCTGCAATTGTTCAAACAG-
CATTTTATTAAATACGCATTACACACCGA
GTAGGGCTATGTAGAGAGGAGTCAGAT-
TATCTACTTAGATTTGGCATCTACTT
AGATYTAACATATACTAGCTGAGAAAT-
TGTAGGCATGTTTGATACACATTTTGAT
TTCAAATGTTTTTCTGTGGATCTGCTTT-
TATTATTTTACAAAAATATNTTTCATACA
AATGGTTAAAAAGAAACAAAATCTATAA-
CAACAACTTTTTGGATTTTTATATATAA
ACTTTTGTGATFFAAATTFACTGAATT-
TAATTAGGGTGAAAATTTTGAAAGTTGT
ATTCTCATATGACTAAGTTCACTAAAAC-
CCTGGATTGAAAGTGAAAATTATGTT
CCTAGAACAAAATGTACAAAAGAA-
CAATATAATTTTCACATGAACCCTTGGCT
GTAGTTGCCTFFCCTAGCTC-
CACTCTAAGGCTAAGCATCTTCAAAGACGTTTTC
CCATATGCTGTCTFAATTCTTTTCACT-
CATTCACCCTTCTTCCCAATCATCTGGCT
GGCATCCTCACAATTGAGTFGAAGCTGT-
TCCTCCTAAAACAATCCTGACTTTTA
TTTTFGCCAAAATCAATACAATC-
CTTTTGAATTTTATCTGCATAAATFTTACAGT
AGAATATGATCAAACCTTCATTTT-
TAAACCTCTCTTCTCTTTTGACAAAACTTCCT
TAAAAAAGAATACAAGATAATATAGG-
TAAATACCCTCCACTCAAGGAGGTAGA
ACTCAGTCCTCTCCCTTGTGAGTCT-
TCACTAAAATCAGTGACTCACTTCCAAAG
AGTGGAGTATGGAAAGGGAAACATAG-
TAACTTTACAGGGGAGAAAAATGACA
AATGACGTCTTCACCAAGTGATCAAAAT-
TAACGTCACCAGTGATAAGTCATTCA
GATTTGTTCTA-
GATAATCTTTCTAAAAATTCATAATC-
CCAATCTAATTATGAGCT
AAAACATCCAGCAAACTCAAGTTGAAG-
GACATTCTACAAAATATCCCTGGGGT
ATTTTAGAGTATTCCTCAAAACTG-
TAAAAATCATGGAAAATAAGGGAATCCTG
AGAAACAATCACAGACCACATGAGAC-
TAAGGAGACATGTGAGCCAAATGCAAT
GTGCTTCTTGGATCAGATCCTGGAACA-
GAAAAAGATCAGTAATGAAAAACTG
ATGAAGTCTGAATAGAATCTGGAG-
TATTTTTAACAGTAGTGTTGATTTCFTAAT
CTTGACAAATATAGCAGGGTAATGTAA-
GATGATAACGTTAGAGAAACTGAAAC
TGGGTGAGGGCTATCTAGGAATTCTCTG-
TACTATCTTACCAAATTTTCGGTAA
GTCTAAGAAAGCAATGCAAAATAAAAAG-
TATCTTGAAAAAAAAAAAAAAAAAA A Table 2: 36P1G3/SGP28 Open Reading Frame (SEQ ID NO: 3)
MKQILHPALETTAMTLFPVLLFLVA-
GLLPSFPANEDICDPAFFALLTTQTQVQREIV
NKHNELRRAVSPPARNMLK-
MEWNKEAAANAQKWANQCNYRHSNP-
KDRMTSLK
CGENLYMSSAPSSWSQAIQSWFDEYND-
FDFGVGPKTPNAVVGHYTQVVWYSSYL
VGCGNAYCPNQKVLKYYYVCQYCPAG-
NWANRLYVPYEQGAPCASCPDNCDDG
LCTNGCKYEDLYSNCKSLKLTLTCK-
HQLVRDSCKASCNCSNSIY

Example 3

SGP28 Gene Expression Analysis

SGP28 mRNA expression in normal human tissues was first analyzed by northern blotting two multiple tissue blots obtained from CLONTECH™ (Palo Alto, Calif.), comprising a total of 16 different normal human tissues, using labeled 36P1G3 cDNA as a probe (sequence as in Example 1). RNA samples were quantitatively normalized with a M-actin probe. The results are shown in FIGS. 1A–B and indicate that, within the 16 tissues tested, the SGP28 gene is exclusively expression in prostate, testis and ovary. Interestingly, the prostate and ovary exhibit a 2.4 kb transcript, while testis expresses a 1.6 kb message (the 1.6 kb message could represent another SGP28 family member). The lower molecular weight signal in normal testis is probably due to cross-hybridization of the probe (SSH fragment) to CRISP2 message. An identical transcript is seen for CRISP2 on this normal panel using a gene specific oligonucleotide probe in the publication by Kratzschmar, J. et al., 1996, Eur. J. Biochem. 236:827–836.

In addition, in order to analyze SGP28 expression in human cancer tissues and cell lines, RNAs derived from LAPC-4 human prostate cancer xenografts were analyzed by northern blot using the 36P1G3 probe. All RNA samples were quantitatively normalized by ethiduim bromide staining and subsequent analysis with a labeled β-actin probe. The results of this analysis are presented in FIG. 1C, and show very high level expression of the 2.4 kb SGP28 transcript in all of the LAPC xenografts.

To analyze SGP28 expression in prostate cancer tissues, northern blotting was performed on RNA derived from three prostate tumor samples with their matched normal adjacent prostate tissue. The results show that SGP28 mRNA expression was detected in all 3 of the 3 tumor specimens tested, and a very high level of expression in 2 of the 3 (FIG. 2).

Example 4

Generation of Polyclonal Antibodies to SGP28

To generate polyclonal sera to SGP28, a peptide was synthesized corresponding to amino acids 93–107 (CNYRHSNPKDRMTSL; SEQ ID NO: 27) of the SGP28 protein. The peptide sequence was coupled to Keyhole limpet hemacyanin (KLH) and was used to immunize a rabbit as follows. The rabbit was initially immunized with 200 μg of peptide-KLH mixed in complete Freund's adjuvant. The rabbit was then injected every two weeks with 200 μg of peptide-KLH in incomplete Freund's adjuvant Bleeds were taken approximately 7–10 days following each immunization. ELISA and western blotting analyses were used to determine specificity and titer of the rabbit serum to the immunizing peptide and SGP28 protein respectively. Affinity purified SGP28 polyclonal antibodies were prepared by passage of crude serum from immunized rabbit over an affinity matrix comprised of SGP28 peptide (CNYRHSNPKDRMTSL; SEQ ID NO: 27) covalently coupled to Affigel 10 (BiORad). After extensive washing of the matrix with PBS, antibodies specific to SGP28 peptide were eluted with low pH glycine buffer (0.1M, pH 2.5), immediately neutralized, and dialyzed extensively against PBS.

Figure 3:
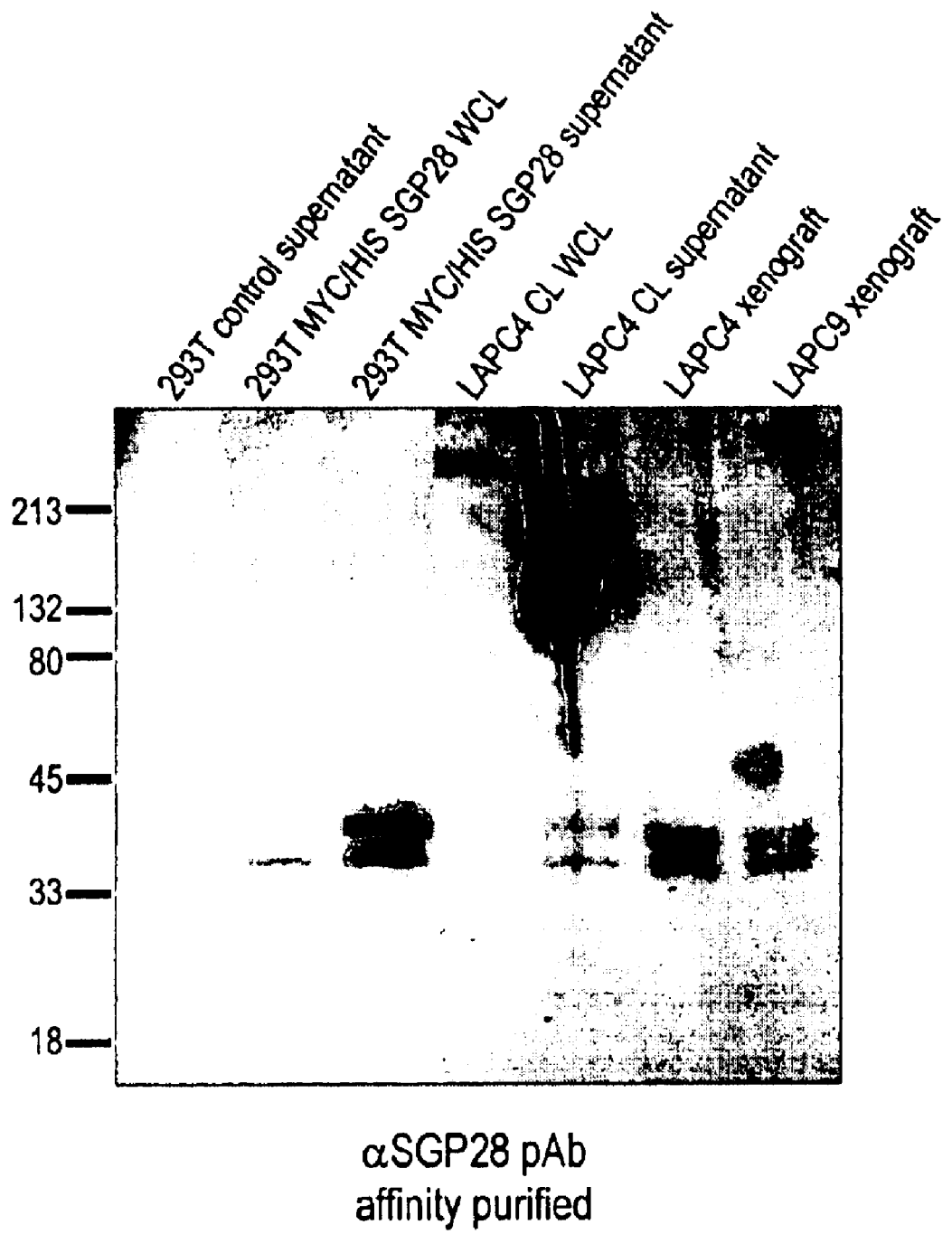
FIG. 3. Western blot demonstrating that anti-SGP28 polyclonal antibody identifies SGP28 protein in LAPC4 and LAPC9 xenograft lysates and in LAPC4 cell line and transfected 293T cell line supernatants. Whole cell lysates (WCL) and supernatants of LAPC4 cells and MYC/HIS SGP28 transiently transfected 293T cells and LAPC4 and LAPC9 xenograft lysates were subjected to western blotting using affinity purified rabbit anti-SGP28 pAb (1 µg/ml). SGP28 immunoreactive bands were visualized by incubation of the blots with HRP-conjugated anti-rabbit secondary antibody, followed by enhanced chemiluminescence detection.

To test the rabbit serum for reactivity with SGP28 protein, full length SGP28 cDNA was cloned into an expression vector that provides a 6His tag at the carboxyl-terminus (pCDNA 3.1 myc-his, InVitrogen). The resulting MYC/HIS SGP28 construct was transfected into 293T cells. Whole cell lysates and supernatants of LAPC4 cells and MYC/HIS SGP28 transiently transfected 293T cells and LAPC4 and LAPC9 xenograft lysates were subjected to western blotting using affinity purified rabbit anti-SGP28 pAb (1 μg/ml). SGP28 immunoreactive bands were visualized by incubation of the blots with HRP-conjugated anti-rabbit secondary antibody, followed by enhanced chemi-luminescence detection. The results are shown in FIG. 3, and demonstrate that the anti-SGP28 polyclonal antibody identifies SGP28 protein in LAPC4 and LAPC9 xenograft lysates and in LAPC4 and transfected 293T cell line supernatants.

Example 5

Expression of Recombinant SGP28 Protein in Mammalian Cells pcDNA3.1/MycHis Construct To express 36P1G3 in mammalian cells, the 774 bp (258 amino acid) 36P1G3 ORF was cloned into pcDNA3.1/MycHis Version A (Onvitrogen, Carlsbad, Calif.). Protein expression is driven from the cytomegalovirus (CMV) promoter. The recombinant protein has the myc and six histidines fused to the C-terminus. The pcDNA3.1/MycHis vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells expressing the protein and the ampicillin resistance gene and ColE1 origin permits selection and maintenance of the plasmid in E. coli.

pAPtag Construct

The 36P1G3/SGP28 protein without the signal sequence (amino acids 33 to 258) was cloned into pAPtag-5 (GenHunter™ Corp. Nashville, Tenn.). This construct generates an alkaline phosphatase fusion at the C-terminus of the 36P1G3 protein while fusing the IgGK signal sequence to N-terminus. The resulting recombinant 36P1G3 protein is optimized for secretion into the media of transfected mammalian cells and can be used to identify proteins such as ligands or receptors that interact with the 36P1G3 protein. Protein expression is driven from the CMV promoter and the recombinant protein also contains myc and six histidines fused to the C-terminus of alkaline phosphatase. The Zeosin resistance gene allows for selection of mammalian cells expressing the protein and the ampicillin resistance gene permits selection of the plasmid in E. coli.

ptag5 Construct

The 36P1G3 protein without the signal sequence (amino acids 33 to 258) was also cloned into pTag-5. This vector is similar to pAPTag but without the alkaline phosphatase fusion.

pSRa Constructs

To generate mammalian cell lines expressing 36P1G3 constitutively, the 774 bp (258 amino acid) ORF was cloned into pSRa constructs. Amphotropic and ecotropic retroviruses are generated by transfection of pSRa constructs into the 293T-10A1 packaging line or co-transfection of pSRa and a helper plasmid (e) in 293 cells, respectively. The retrovius can be used to infect a variety of mammalian cell lines, resulting in the integration of the cloned gene, 36P1G3, into the host cell-lines. Protein expression is driven from a long terminal repeat (LTR). The neomycin resistance gene allows for selection of mammalian cells expressing the protein and the ampicillin resistance gene and ColE1 origin permits selection and maintenance of the plasmid in E. coli.

An additional pSRa construct was made that fused the FLAG tag to the C-terminus to allow detection using anti-FLAG antibodies. The FLAG sequence 5' gat tac aag gat gac gac gat aag 3' (SEQ ID NO: 36) were added to cloning primer at the 3' end of the ORF.

Additional pSRa constructs can be made to produce both N-terminal and C-terminal GFP and myc/6 HIS fusion proteins of the full length 36P1G3 protein.

Example 6

Expression of Recombinant SGP28 Protein in Insect Cells pMelBac a

The 36P1G3 protein without the signal sequence (amino acids 33 to 258) was also cloned into pMelBac (Cat no. VI 950-20, Invitrogen, CA) to express and secrete the protein in Sf9 insect cells. The pMelBAC A vector is a baculovirus transfer vector designed to direct expression of recombinant proteins through the secretory pathway to the extracellular medium. The signal sequence for honeybee melittin, a high expressed and efficiently secreted protein, is used to direct secretion of the recombinant 36P1G3 protein. Protein expression is driven under the polyhedrin promoter. A C-terminal myc-his tagged construct was also made in pMelBac A to allow for detection and purification of the recombinant 36P1G3 protein.

pIZT/V5His

The 36P1G3 protein was cloned into pIZT/V5His (Cat no. v8010-01, Invitrogen, CA) to express the protein in Sf9 insect cells. The expression vector allows for transient and stable expression of the recombinant protein. Protein expression is driven by the OpIE2 promoter for high-level, constitutive expression. The Zeocin resistance gene is under the control of the OpIE1 promoter.

Example 7

Production of Monoclonal Antibodies to SGP28

To generate mAbs to SGP28, recombinant HIS-tagged SGP28 protein purified from 293T tissue culture supernatants was used to immunize 5 female Balb C mice. Initial immunization was carried out with 50 μg of purified SGP28 protein mixed in Freund's complete adjuvant. Boosts were then administered in 2 week intervals with 50 μg of SGP28 protein mixed in Freund's incomplete adjuvant. Reactivity and specificity of test bleeds taken 7–10 days following each immunization was determined by ELISA and western blotting procedures. The specific titer of test bleeds to the immunogen was at least $2 \times 10^6$. Three mice were subsequently sacrificed and spleens were used to carry out fusion and hybridoma generation using standard procedures (Harlow and Lane, 1988). Eleven positive wells were then subjected to subcloning to generate SGP28-specific monoclonal hybridomas. One of the hybridomas that has completed subcloning, designated 4G6 (IgG1 isotype), specifically recognizes SGP28 protein present in prostate cancer cell lysates and supernatants and markedly reacts with SGP28 protein in clinical prostate cancer tissue, but not in normal adjacent tissue from the same patient (FIG. 4).

Figure 4:
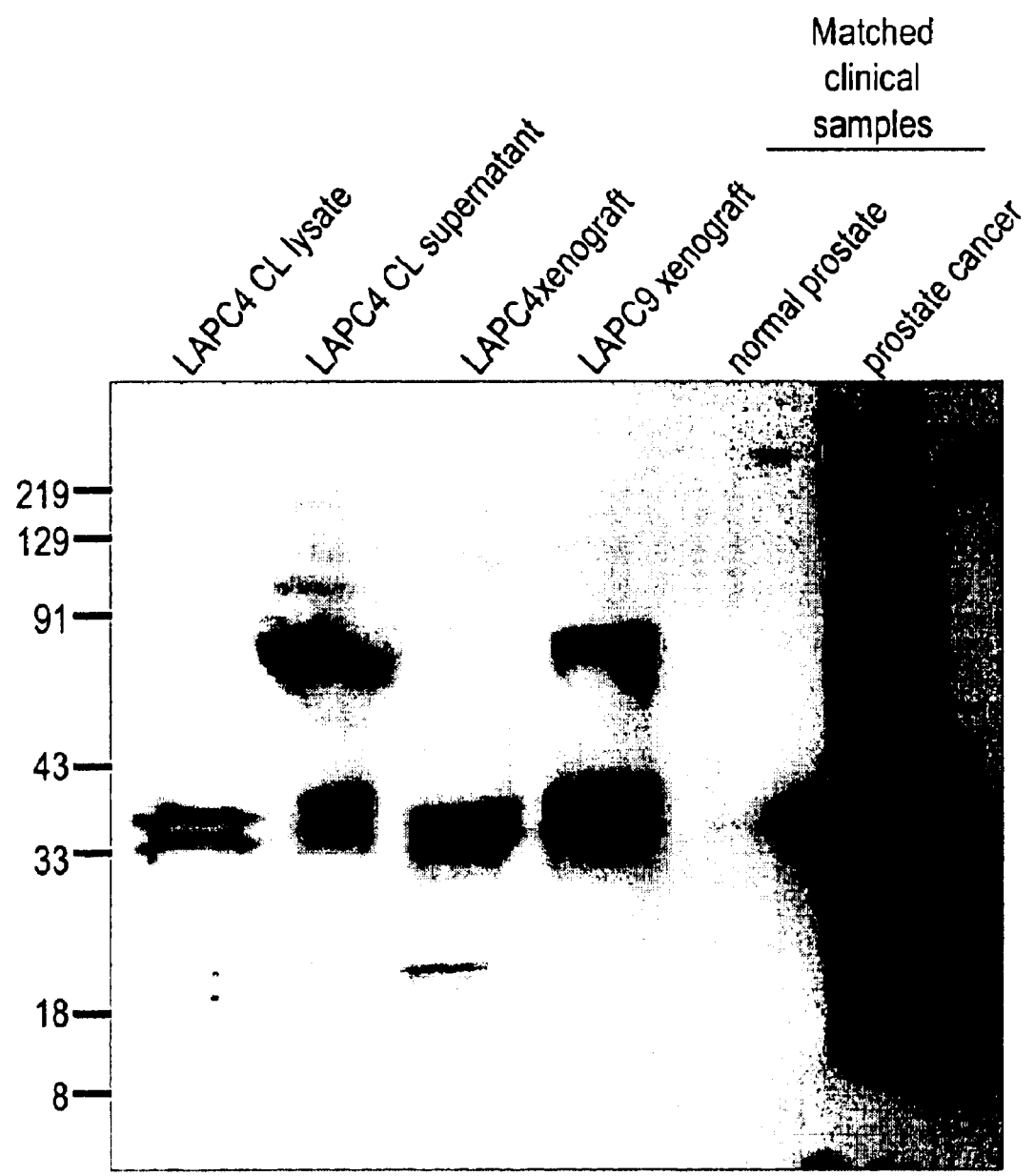
FIG. 4. Western blot analysis showing that ant-SGP28/CRISP-3 monoclonal antibody specifically detects SGP28/CRISP-3 protein in prostate cancer cell lines and supernatants, prostate cancer xenografts, and clinical prostate cancer tissue. Cell lysate and conditioned media from the LAPC4 prostate cancer cell line and lysates from LAPC4 and LAPC9 prostate cancer xenografts and from a matched normal and cancerous prostate clinical specimen were separated by SDS-PAGE and transferred to nitrocellulose. The blot was then subjected to western analysis with a 1:2 dilution of 4G6 anti-SGP28/CRISP-3 monoclonal antibody supernatant. Specific SGP28/CRISP-3 immunoreactive bands were then visualized by incubation with anti-mouse IgG-HRP conjugate secondary antibody and development with enhanced chemiluminescence and exposure to autoradiographic film.

FIG. 4 shows that anti-SGP28 monoclonal antibody specifically detects SGP28 protein in prostate cancer cell lines and supernatants, prostate cancer xenografts, and clinical prostate cancer tissue. Cell lysate and conditioned media from the LAPC4 prostate cancer cell line and lysates from LAPC4 and LAPC9 prostate cancer xenografts and from a matched normal and cancerous prostate clinical specimen were separated by SDS-PAGE and transferred to nitrocellulose. The blot was then subjected to western analysis with a 1:2 dilution of 4G6 anti-SGP28 monoclonal antibody supernatant. Specific SGP28 immunoreactive bands were then visualized by incubation with anti-mouse IgG-HRP conjugate secondary antibody and development with enhanced chemiluminescence and exposure to autoradiographic film. Indicated with arrows is the SGP28 immunoreactive protein doublet.

Example 9

Western Analysis of SGP28 Protein Expression

Figure 5A:
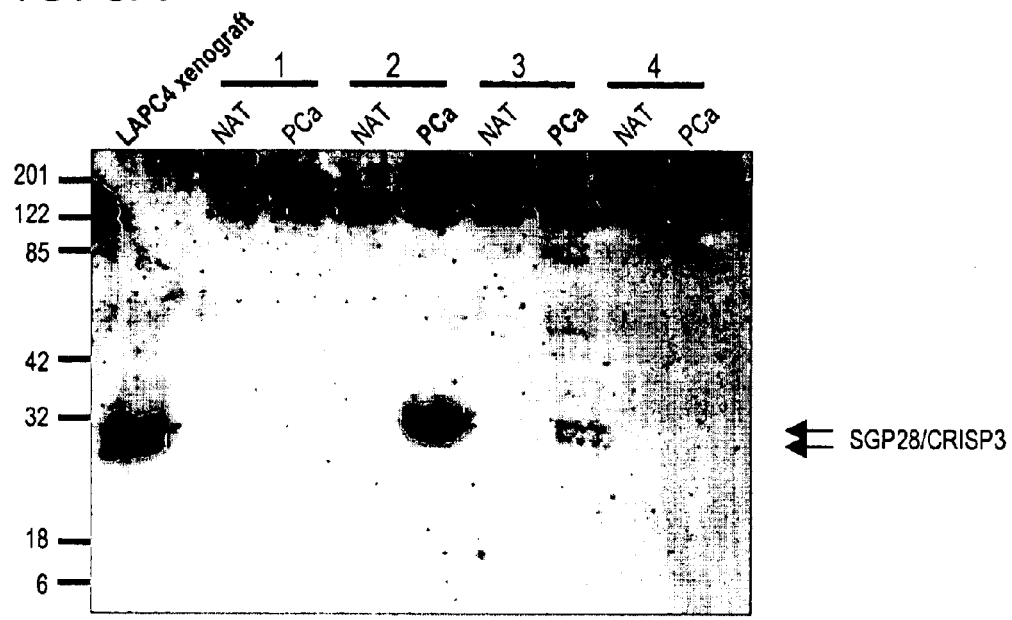
FIG. 5A. Western blot analysis showing high level expression of SGP28 in prostate cancer clinical samples and LAPC xenografts. Matched clinical tissue lysates of prostate cancer (PCa) and normal adjacent tissue NAT) and of LAPC4 xenograft were subjected to western blotting with 1 µg/ml of affinity purified rabbit anti-SGP28 pAb. SGP28 immunoreactive bands were visualized by incubation of the blots with HRP-conjugated anti-rabbit secondary antibody followed by enhanced chemiluminescence detection. Indicated with arrows is the SGP28/CRISP-3 immunoreactive protein doublet.
Figure 5B:
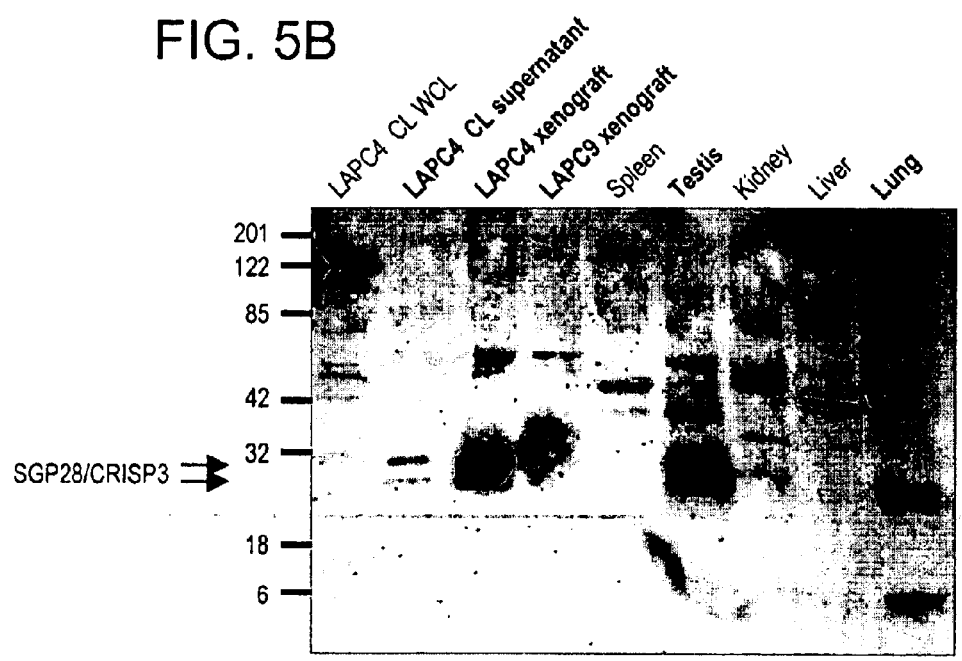
FIG. 5B. Western blot analysis showing high level expression of SGP28 in LAPC xenografts and low level expression in normal testis and lung. Normal tissue lysates of spleen, testis, kidney, liver and lung, and LAPC4 cell line and xenograft were subjected to western blotting as described for FIG. 5A. Indicated with arrows is the SGP28/CRISP-3 immunoreactive protein doublet.

Matched clinical tissue lysates of prostate cancer and normal adjacent tissue, as well as a normal tissue lysates of an LAPC4 cell line and LAPC-4 xenograft were subjected to western blotting with 1 μg/ml of affinity purified rabbit anti-SGP28 polyclonal antisera. SGP28 immunoreactive bands were visualized by incubation of the blots with HRP-conjugated anti-rabbit secondary antibody followed by enhanced chemiluminescence detection. The results (FIGS. 5A–B) show high level expression of SGP28 in the prostate cancer samples but not the adjacent normal tissue and high level expression in the LAPC xenografts. Low level expression was detected in normal testis and lung.

Example 10

Figure 6A:
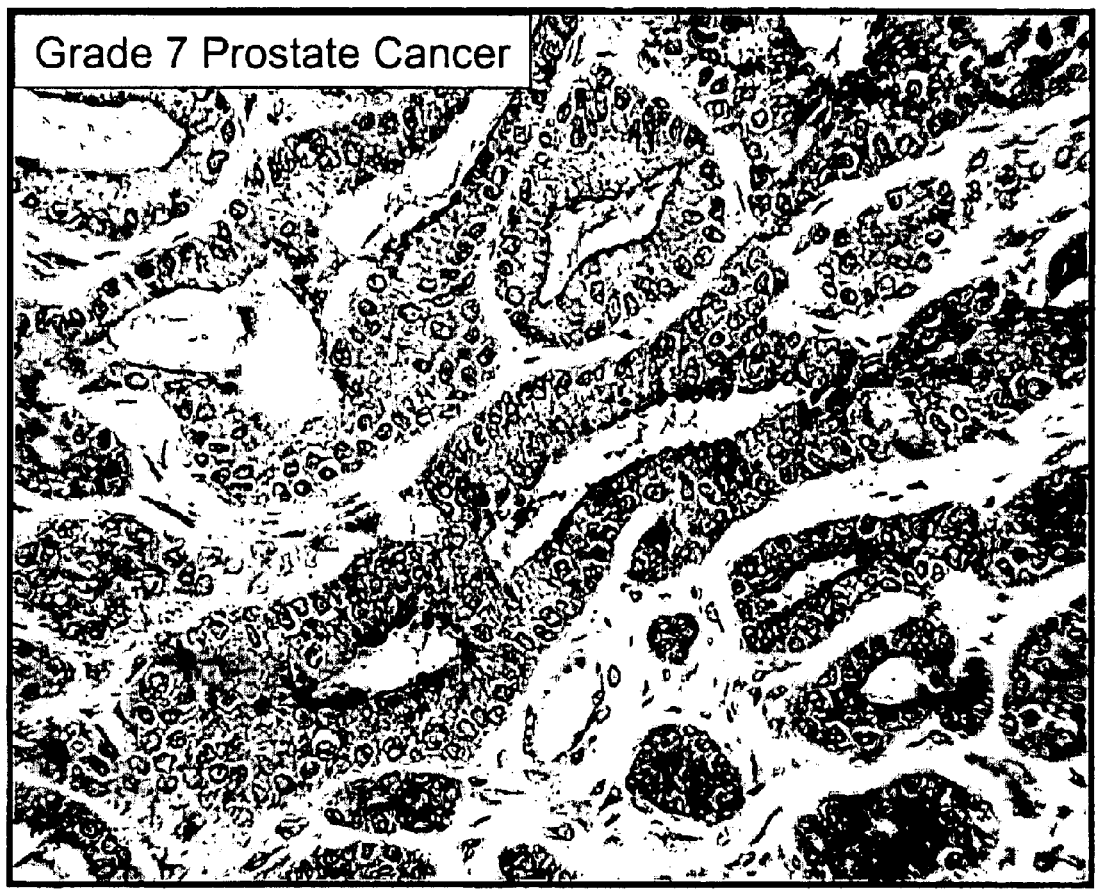
FIGS. 6A–B. Immunohistochemical analysis of SGP28 protein in Gleason score 7 prostate cancer (FIG. 6A) and high grade PIN (FIG. 6B), showing high level expression and secretion of SGP28 into the lumen of the prostate gland, using affinity purified polyclonal antibody. Strong staining was observed in the epithelial cells of the prostate gland, especially at the lumenal borders. Staining was also observed within the lumen) indicating high level expression and secretion of SGP28 in prostate cancer and PIN.
Figure 6B:
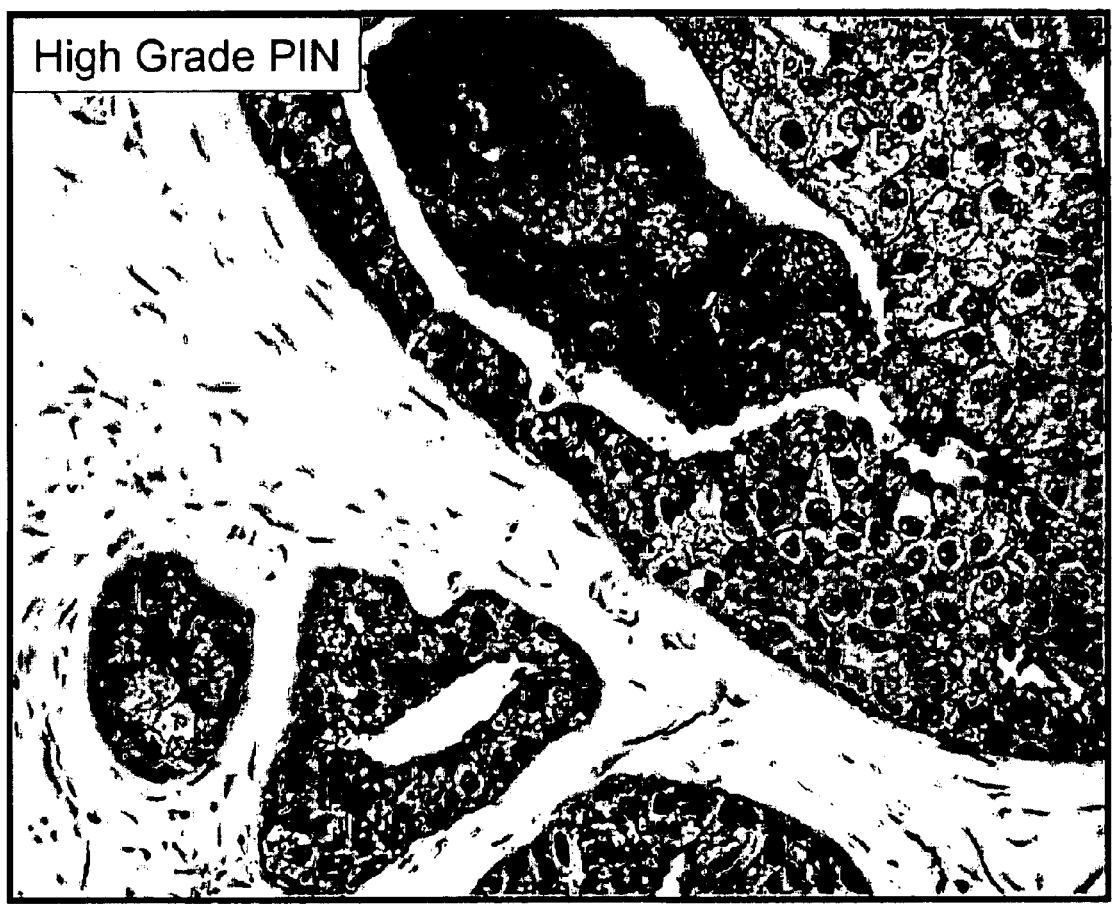

Immunohistochemical Detection of SGP28 in Prostate Cancer, PIN and Prostate Cancer Metastases SGP28 expression in a Gleason score 7 prostate cancer specimen as well as a high grade PIN specimen were subjected to immunohistochemical analysis of SGP28 expression as follows. Tissue sections were prepared from the samples, were fixed in 10% formalin, embedded in paraffin, and sectioned according to standard protocol. Sections were stained with an anti-SGP28 polyclonal antibody (as described above). The results are shown in FIGS. 6A–B. Strong staining was observed in the epithelial cells of the prostate gland, especially at the lumenal borders. Staining was also observed within the lumen, indicating high level expression and secretion of SGP28 in prostate cancer and PIN.

Figure 7A:
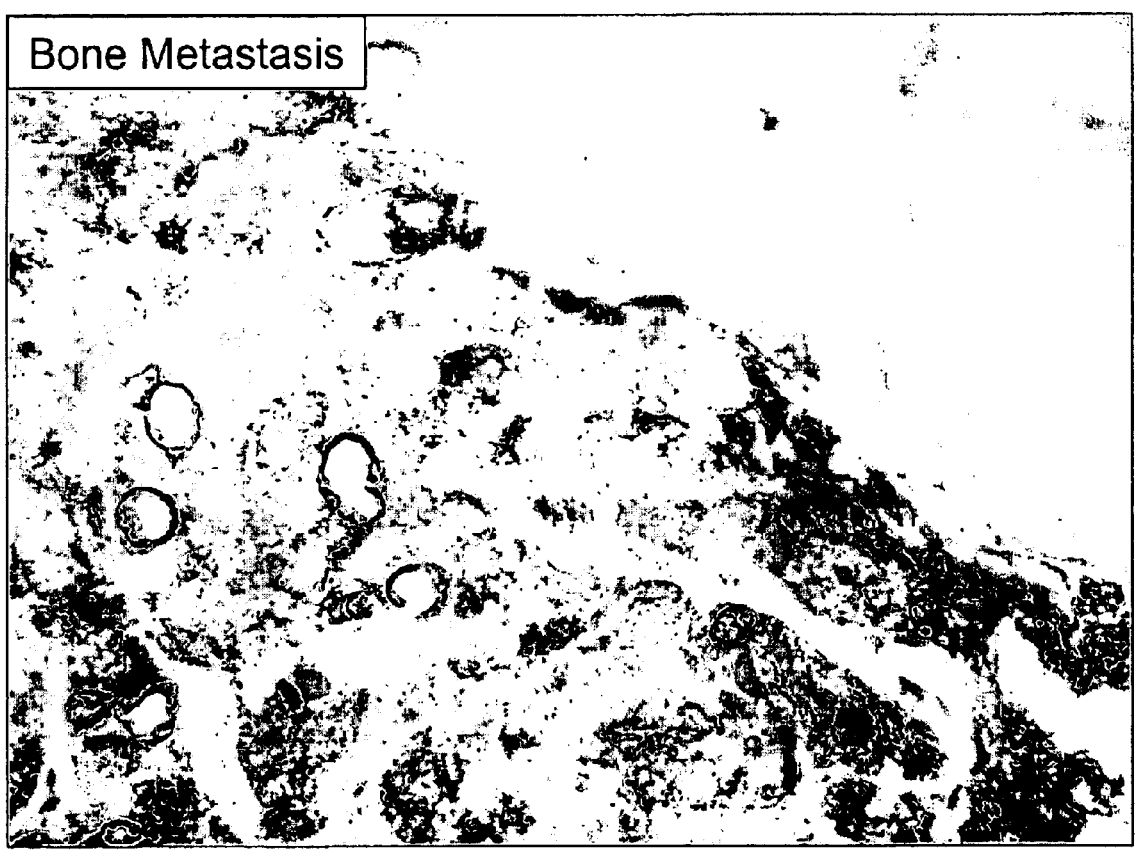
FIGS. 7A–B. Immunohistochemical analysis demonstrating SGP28 protein expression in prostate cancer metastases to bone (FIG. 7A) and lymph node (FIG. 7B), FIGS. 8A–D. Immunohistochemical analysis of SGP28 protein in prostate cancer and PIN. FIG. BA shows immunohistochemical detection of SGP28 in prostate cancer at a magnification of 200×.
Figure 7B:
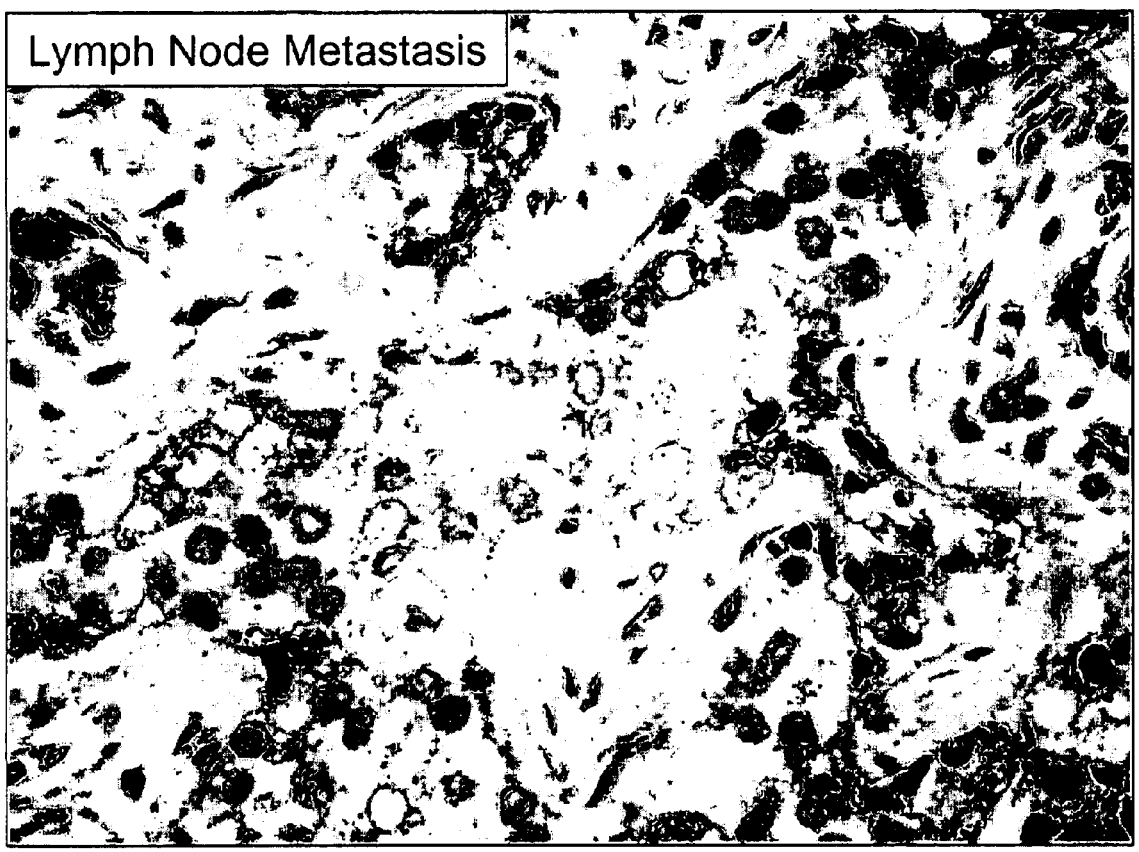

Similarly, polyclonal anti-SGP28 was used to assess the ability to detect SGP28 expression in prostate cancer metastases. FIGS. 7A–B show the results of immunohistochemical analysis demonstrating SGP28 protein expression in prostate cancer metastases to bone (FIG. 7A) and lymph node (FIG. 7B).

The high expression of SGP28 in prostate cancer and PIN was further demonstrated using immunohistochemistry, and the results are shown in FIGS. 8A–D. FIG. 8A shows immunohistochemical detection of SGP28 in prostate cancer at a magnification of 200×; FIG. 8B shows the same at 800×. SGP28 expression in PIN is shown in FIG. 8C at 200×, and in FIG. 8D at 800×. A summary of the results of immunohistochemical analysis is shown in Table 3 for prostate cancer and PIN, and in Table 4 for a wider range of tissues. The lack of immunohistochemically detectable expression in the wide range of tissues examined, including normal prostate, combined with strong staining in prostate cancer and PIN, indicates that SGP28 is a particularly suitable target for antibody-based diagnostics, including evaluation of biopsy specimens and in vivo imaging.

TABLE 3

Immunohistochemistry Summary for Prostate Cancer and PIN

| Tissue | Staining | Intensity |
|---|---|---|
| Normal prostate/BPH | 0/14 | None |
| PIN | 1/1 | Strong |
| Prostate cancer | 6/9 | Strong |
| Lymph node metastases | 4/5 | Moderate to strong |
| Bone metastatases | 2/4 | Moderate to strong |

TABLE 4

Immunohistochemistry Summary for Human Tissues

| Staining intensity | Tissue |
|---|---|
| None | Prostate (8/8) |
| | BPH (6/6) |
| | Pancreas |
| | Liver |
| | Lung |
| | Testis |
| | Colon |
| | Spleen |
| | Cerebellum |
| | Heart |
| | Kidney |
| Light | Fallopian tubes |
| | Colon cancer |
| | Salivary glands |
| Moderate to strong | PIN (1/1) |
| | Prostate cancer (6/9) |
| | Lymph node mets (4/5) |
| | Bone mets (2/4) |

Example 11

Identification of Potential Signal Transduction Pathways

To determine whether SGP28 directly or indirectly activates known signal transduction pathways in cells, luciferase (luc) based transcriptional reporter assays are carried out in cells expressing SGP28. These transcriptional reporters contain consensus binding sites for known transcription factors which lie downstream of well characterized signal transduction pathways. The reporters and examples of there associated transcription factors, signal transduction pathways, and activation stimuli are listed below.
1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress SGP28-mediated effects may be assayed in cells showing mRNA expression. Luciferase reporter plasmids may be introduced by lipid mediated transfection (TFX-50. Promega™). Luciferase activity, an indicator of relative transcriptional activity, is measured by incubation of cells extracts with luciferin substrate and luminescence of the reaction is monitored in a luminometer.

Example 12

In Vitro Assays of SGP28 Function

The expression profile of SGP28 in prostate cancer suggests a functional role in tumor initiation, progression and/or maintenance. SGP28 function can be assessed in mammalian cells using in vitro approaches. For mammalian expression, SGP28 can be cloned into a number of appropriate vectors, including pcDNA 3.1 myc-His-tag and the retroviral vector pSRαtkneo (Muller et al., 1991, MCB 11:1785). Using such expression vectors, SGP28 can be expressed in several cancer cell lines, including for example PC-3, NIH 3T3, LNCaP and 293T. Expression of SGP28 can be monitored using anti-SGP28 antibodies.

Mammalian cell lines expressing SGP28 can be tested in several in vitro and in vivo assays, including cell proliferation in tissue culture, activation of apoptotic signals, primary and metastatic tumor formation in SCID mice, and in vitro invasion using a membrane invasion culture system (MICS) (Welch et al., Int J. Cancer 43: 449–457). SGP28 cell phenotype is compared to the phenotype of cells that lack expression of SGP28. In addition, cells treated with and without exogenously added SGP28 protein may be analyzed for altered growth parameters.

Cell lines expressing SGP28 can also be assayed for alteration of invasive and migratory properties by measuring passage of cells through a matrigel coated porous membrane chamber (Becton Dickinson™). Passage of cells through the membrane to the opposite side is monitored using a fluorescent assay (Becton Dickinson Technical Bulletin #428) using calcein-Am (Molecular Probes) loaded indicator cells. Cell lines analyzed include parental and SGP28 overexpressing PC3, 3T3 and LNCaP cells. To assay whether SGP28 has chemoattractant properties, parental indicator cells are monitored for passage through the porous membrane toward a gradient of SGP28 conditioned media compared to control media. This assay may also be used to qualify and quantify specific neutralization of the SGP28 induced effect by candidate cancer therapeutic compositions.

In order to establish whether SGP28 binds to cellular proteins expressed in prostate run cancer cells and other cancer cells or normal cells, two approaches may be taken. In the first approach, in vitro assay for recombinant HIS-tagged SGP28 binding to various cell lines are used. In another approach, a recombinant alkaline phosphatase-SGP28 fusion protein is generated using the AP-TAG system from GenHunter Corporation (Nashville, Tenn., cat# Q202), and the AP-TAG fusion used to test SGP28 binding to a variety of prostate cancer cell lines as described (Cheng and Flanagan, 1994, Cell 79:157–168). After washing the cells and adding the AP substrate BCIP, which forms an insoluble blue precipitate upon dephosphorylation, SGP28 binding is determined by identifying cells staring blue under the light microscope. Various cancer cell lines can be examined, including without limitation, various prostate cancer cell lines (e.g., LNCaP, PC-3, DU145, TSUPR, LAPC4). Other cell lines such as PREC prostate cell line, 293T, PIN cells, and NIH 3T3, etc. may also be examined. Additionally, the LAPC and other prostate cancer xenografts may be tested. Equilibrium dissociation rate constants may be calculated to evaluate the strength of the binding interaction. In addition, the number of cell surface receptors per cell can be determined. Cell lines or tissues with the highest binding capacity for SGP28 would be preferred for cloning the SGP28 receptor or other binding partner.

In another functional assay, N1H-3T3 cells stably expressing SGP28 can be analyzed for their ability to form colonies in soft agar. In these experiments, cells used in such procedures (e.g. NIH-3T3 cells), can be transfected to stably express SGP28 or neo or activated-Ras (as the test gene, the negative and the positive controls, respectively) in order to assess the transforming capabilities of SGP28. Typically experiments are performed in duplicate and the assays are evaluated approximately 4 weeks after cell plating. Where experimental observations demonstrate that SGP28 induces an increase in colony formation relative to a negative control (e.g. neo) such results indicate that SGP28 has significant transforming capabilities.

Example 13

In Vivo Assay for SGP28 Tumor Growth Promotion

The effect of the SGP28 protein on tumor cell growth may be evaluated in vivo by gene overexpression in tumor-bearing mice. For example, SCID mice can be injected SQ on each flank with $1 \times 10^6$ of a prostate cell line containing tkNeo empty vector or SGP28. At least two strategies may be used: (1) Constitutive SGP28 expression under regulation of an LTR promoter, and (2) Regulated expression under control of an inducible vector system, such as ecdysone, tet, etc. Tumor volume is then monitored at the appearance of palpable tumors and followed over time to determine if SGP28 expressing cells grow at a faster rate. Additionally, mice may be implanted with $1 \times 10^5$ of the same cells orthotopically to determine if SGP28 has an effect on local growth in the target tissue (i.e., prostate) or on the ability of the cells to metastasize, specifically to lungs, lymph nodes, liver, bone marrow, etc. The effect of SGP28 on bone tumor formation and growth may be assessed by injecting prostate tumor cells intratibially, as described in Example 1.

These assays are also useful to determine the SGP28 inhibitory effect of candidate therapeutic compositions, such as for example, SGP28 antibodies, SGP28 antisense molecules and ribozymes.

Example 14

Functional Assays for Binding of SGP28 to Cells

Several secreted proteins have been described in prostate cancer, a number of which have been shown to participate in the process of tumor formation and progression (Inoue K., 2000, Clin. Cancer Res. 6:2104–19, Dow J K, deVere White R W, 2000, Urology 55:800–6). As SGP28 is a secreted protein, one of its potential functions is to regulate the microenvironment of prostate cancer and of metastatic disease. In order to test this possibility, SGP28 can be expressed and purified as a recombinant protein, such as GST-SGP28 or SGP28-Myc/His. Purified recombinant-SGP28 (whether GST-SGP28 or SGP28-Myc/His) is then incubated with a variety of cell types that recapitulate the environment of the prostate, including prostate epithelial cells, prostate tumor cell lines, prostate stromal cells, prostate endothelial cells and prostate neuroendocrine cells. In addition, recombinant-SGP28 is also incubated with cells found at metastatic sites, such as bone marrow cells and cells of the immune system. Binding of SGP28 to intact cells is detected by FACS analysis and by calorimetric assay. This analysis is valuable as it identifies with a cell population that binds and may respond to SGP28. In addition, the identification of a target cell population provides a means of isolating and identifying SGP28 receptors, thereby providing additional means of modulating SGP28-mediated events.

Example 15

Assays for Defensin-like Activity of SGP28

SGP28 has a strong homology to defensin proteins, in particular to beta-defensins.

Beta-defensins are secreted products mainly produced by epithelial cells (O'Neil D A et al, 1999, J. Immunol. 163:6718–24; Schroder J M, Harder J., 1999, Int. J. Biochem. Cell. Biol. 31:645–51). Defensins play an important role in preventing infections and safeguarding the immunity of epithelial tissues. In addition, the human HNP1 defensin has been shown to induce the death of tumor cells in vitro. Investigating the role of SGP28 in cell death, purified recombinant-SGP28 is incubated with a variety of cell types listed above and analyzed for apoptotic activity using FACS analysis of Annexin V stained cells. SGP28 may also function as a chemoattractant, as has been shown for other defensin molecules (Yang D et al., 2000, Leukoc. Biol. 68:9–14; Yang D et al., 1999, Science 286(5439):525–8.). Using a chemotactic assay, one can evaluate the effect of SGP28 on the migration of various types of cells, including epithelial, stromal, endothelial cells as well as monocytes, lymphocytes and dendritic cells.

Example 16

Predicted Binding of SGP28 Peptides to HLA-A2

To identify SGP28 peptides predicted to bind to the human MHC class I molecule HLA-A2, the complete amino acid sequence of the SGP28 protein was entered into the HLA Peptide Motif Search algorithm found in the Bioinformatics and Molecular Analysis Section (BIMAS) Web site. The results of SGP28 predicted binding peptides are shown in Table 5. The top 10 ranking candidates are shown along with their location, the amino acid sequence of each specific peptide, and an estimated binding score. The binding score corresponds to the estimated half-time of dissociation of complexes containing the peptide at 37° C. at pH 6.5. Peptides with the highest binding score (i.e., 999.9 for SGP28 peptide 2) are predicted to be the most tightly bound to HLA Class I on the cell surface and thus represent the best immunogenic targets for T-cell recognition. Actual binding of peptides to HLA-A2 can be evaluated by stabilization of HLA-A2 expression on the antigen-processing defective cell line T2 (Xue et al., 1997, Prostate 30:73–8; Peshwa et al., 1998, Prostate 36:129–38). Immunogenicity of specific peptides can be evaluated in vitro by stimulation of CD8+ cytotoxic T lymphocytes (CTL) in the presence of dendritic cells (Xue et al., 1997, Prostate 30:73–8; Peshwa et al., 1998, Prostate 36:129–38).

TABLE 5

| | SGP28 Peptides Having Highest Predicted Binding Scores | | |
|---|---|---|---|
| Rank | Start Position | Subsequence Residue Listing | Score (Estimate of half time of disassociation) |
| 1 | 2–10 | TLFPVLLFL (SEQ ID NO: 17) | 999.9 |
| 2 | 6–14 | VLLFLVAGL (SEQ ID NO: 18) | 309.1 |
| 3 | 30–38 | ALLTTQTQV (SEQ ID NO: 19) | 257.3 |
| 4 | 142–150 | VVWYSSYLV (SEQ ID NO: 20) | 85.9 |

TABLE 5-continued

SGP28 Peptides Having Highest Predicted Binding Scores

| Rank | Start Position | Subsequence Residue Listing | Score (Estimate of half time of disassociation) |
|---|---|---|---|
| 5 | 222–230 | TLTCKHQLV (SEQ ID NO: 21) | 69.6 |
| 6 | 175–183 | GNWANRLYV (SEQ ID NO: 22) | 20.7 |
| 7 | 7–15 | LLFLVAGLL (SEQ ID NO: 23) | 17.5 |
| 8 | 141–149 | QVVWYSSYL (SEQ ID NO: 24) | 10.3 |
| 9 | 134–142 | AVVGHYTQV (SEQ ID NO: 25) | 9.1 |
| 10 | 211–219 | DLYSNCKSL (SEQ ID NO: 26) | 5.1 |

Throughout this application, various publications are referenced. The disclosures of publications are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. An isolated polynucleotide selected from the group consisting of:
   (a) a polynucleotide comprising the sequence as shown in Table 1 (SEQ ID NO: 2), or a polynucleotide comprising the sequence as shown in Table 1 (SEQ ID NO: 2) wherein every T is replaced by U; and
   (b) a polynucleotide comprising the sequence as shown in Table 1 (SEQ ID NO: 2), from nucleotide residue number 3 through nucleotide residue number 776, or a polynucleotide comprising the sequence as shown in Table 1 (SEQ ID NO: 2), from nucleotide residue number 3 through nucleotide residue number 776 wherein every T is replaced by U.

2. An isolated polynucleotide wherein the polynucleotide is fully complementary to a polynucleotide of claim 1.

3. An isolated polynucleotide fragment of the sequence as shown in Table 1 (SEQ ID NO: 2) or the full complement thereof, or an isolated polynucleotide fragment of the sequence as shown in Table 1 (SEQ ID NO: 2) or the full complement thereof wherein every T is replaced by U, which fragment encodes a peptide of nine or ten amino acids wherein said peptide is a fragment of SEQ ID NO:3,
   wherein said peptide binds to an HLA class I molecule and wherein said peptide is capable of eliciting the production of an antibody that binds specifically to the polypeptide of SEQ ID NO: 3 or wherein said polynucleotide fragment is capable of specifically hybridizing to the nucleic acid molecule of SEQ ID NO: 2 or its full complement.

4. An isolated polynucleotide fragment of the sequence as shown in Table 1 (SEQ ID NO: 2) from nucleotide residue number 3 through nucleotide residue number 776 or the full complement thereof, or an isolated polynucleotide fragment of the sequence as shown in Table 1 (SEQ ID NO: 2) from nucleotide residue number 3 through nucleotide residue number 776 or the full complement thereof wherein every T is replaced by U, which fragment encodes a peptide of nine or ten amino acids wherein said peptide is a fragment of SEQ ID NO: 3,
   wherein said polypeptide binds to an HLA class I molecule and wherein said peptide is capable of eliciting the production of an antibody that binds specifically to the polypeptide of SEQ ID NO: 3 or wherein said polynucleotide fragment is capable of specifically hybridizing to the nucleic acid molecule of SEQ ID NO: 2 or its full complement.

5. An isolated polynucleotide selected from the group consisting of:
   a polynucleotide encoding an amino acid sequence consisting of SEQ ID NO: 17;
   a polynucleotide encoding an amino acid sequence consisting of SEQ ID NO: 18;
   a polynucleotide encoding an amino acid sequence consisting of SEQ ID NO: 19;
   a polynucleotide encoding an amino acid sequence consisting of SEQ ID NO: 20,
   a polynucleotide encoding an amino acid sequence consisting of SEQ ID NO: 21;
   a polynucleotide encoding an amino acid sequence consisting of SEQ ID NO: 22;
   a polynucleotide encoding an amino acid sequence consisting of SEQ D NO: 23;
   a polynucleotide encoding an amino acid sequence consisting of SEQ ID NO: 24;
   a polynucleotide encoding an amino acid sequence consisting of SEQ ID NO: 25;
   a polynucleotide encoding an amino acid sequence consisting of SEQ ID NO. 26; and,
   a polynucleotide encoding an amino acid sequence consisting of SEQ ID NO: 27.

6. An isolated polynucleotide wherein the polynucleotide is fully complementary to a polynucleotide of claim 5.

\* \* \* \* \*